US006268484B1

(12) United States Patent
Katinger et al.

(10) Patent No.: US 6,268,484 B1
(45) Date of Patent: Jul. 31, 2001

(54) HIV-VACCINES

(75) Inventors: Hermann Katinger; Andrea Buchacher; Wolfgang Ernst; Claudia Ballaun; Martin Purtscher; Alexandra Trkola, all of Vienna; Renate Predl, Deutsch-Wagram; Christine Schmatz, Vienna; Annelies Klima, Vienna; Franz Steindl, Vienna; Thomas Muster, Vienna, all of (AT)

(73) Assignee: Polymun Scientific Immunbiologische Forschung GmbH, Vienna (AT)

( * ) Notice: Subject to any disclaimer, the term of this patent is extended or adjusted under 35 U.S.C. 154(b) by 0 days.

(21) Appl. No.: 09/124,900

(22) Filed: Jul. 30, 1998

Related U.S. Application Data

(60) Division of application No. 08/478,536, filed on Jun. 7, 1995, now Pat. No. 5,911,989, which is a continuation-in-part of application No. PCT/EP95/01481, filed on Apr. 19, 1995.

(51) Int. Cl.[7] .......................... C07K 16/00; A61K 39/00; A61K 39/21; C12Q 1/70; G01N 33/53
(52) U.S. Cl. ................... 530/388.35; 424/192.1; 424/208.1; 435/5; 435/7.1; 435/339.1
(58) Field of Search ................... 424/192.1, 208.1; 530/388.35; 435/5, 7.1, 339.1

(56) References Cited

U.S. PATENT DOCUMENTS 4,761,470   8/1988   Emini et al. .................. 530/326
5,087,557   2/1992   McClure ....................... 435/5
5,245,015   9/1993   Fung et al. ................. 530/388.35
5,516,657   5/1996   Murphy et al. ................ 435/69.3

OTHER PUBLICATIONS

Fahey et al., Status of immune–based therapies in HIV infection and AIDS Clin. Exp. Immunol. (1992) 88, 1–5 01/92.

Luckow et al., Trends in the development of Baculovirus expression vectors, Bio/Tech vol. 6, pp. 47–55, see Abstract and p. 47, col. 1, sentence 4. (01/88).

Ratner et al., Complete nucleotide sequence of the AIDS virus, HTLV–III, Nature 313:277–284 (01/85).

Primary Examiner—Hankyel Park
(74) Attorney, Agent, or Firm—Birch, Stewart, Kolasch & Birch, LLP.

(57) ABSTRACT

Disclosed are antibodies which can be used for the manufacture of vaccines for active and/or passive immunization of persons in need of such treatment. The invention also provides for human monoclonal antibodies that are functionally equivalent to the above-mentioned antibodies produced by any one of the cell lines CL1 through CL6 (deposited at the European Collection of Animal Cell Cultures (ECACC) at the PHLS in Porton Down, Salisbury, UK). Also provided are hybridoma and/or CHO cell lines producing any one of the antibodies disclosed and claimed herein, Also provided are mixtures of antibodies of the present invention, as well as methods of using individual antibodies or mixtures thereof for the detection, prevention and/or therapeutical treatment of HIV-1 infections in vitro and in vivo.

8 Claims, 6 Drawing Sheets

SEQUENCE LISTING

<160> NUMBER OF SEQ ID NOS: 11

<210> SEQ ID NO 1
<211> LENGTH: 8932
<212> TYPE: DNA
<213> ORGANISM: Human imunodeficiency virus type 1

<400> SEQUENCE: 1

```
agctctctcg acgcaggact cggcttgctg aagcgcgcac ggcaagaggc gaggggcggc        60
gactggtgag tacgccaaaa attttgacta gcggaggcta gaaggagaga gatgggtgcg       120
agagcgtcag tattaagcgg gggagaatta gatcgatggg aaaaaattcg gttaaggcca       180
gggggaaaga aaaaatataa attaaaacat atagtatggg caagcaggga gctagaacga       240
ttcgcagtta atcctggcct gttagaaaca tcagaaggct gtagacaaat actgggacag       300
ctacaaccat cccttcagac aggatcagaa gaacttagat cattatataa tacagtagca       360
accctctatt gtgtgcatca aaggatagag ataaaagaca ccaaggaagc tttagacaag       420
atagaggaag agcaaaacaa aagtaagaaa aaagcacagc aagcagcagc tgacacagga       480
cacagcagtc aggtcagcca aaattaccct atagtgcaga acatccaggg gcaaatggta       540
catcaggcca tatcacctag aactttaaat gcatgggtaa aagtagtaga agagaaggct       600
ttcagcccag aagtaatacc catgttttca gcattatcag aaggagccac cccacaagat       660
ttaaacacca tgctaaacac agtggggggga catcaagcag ccatgcaaat gttaaaagag       720
accatcaatg aggaagctgc agaatgggat agagtacatc cagtgcatgc agggcctatt       780
gcaccaggcc agatgagaga accaagggga agtgacatag caggaactac tagtacccctt     840 caggaacaaa taggatggat gacaaataat ccacctatcc cagtaggaga aatttataaa       900
```

-continued

```
agatggataa tcctgggatt aaataaaata gtaagaatgt atagccctac cagcattctg    960
gacataagac aaggaccaaa agaaccttt agagactatg tagaccggtt ctataaaact   1020
ctaagagccg agcaagcttc acaggaggta aaaaattgga tgacagaaac cttgttggtc   1080
caaaatgcga acccagattg taagactatt ttaaaagcat tgggaccagc ggctacacta   1140
gaagaaatga tgacagcatg tcagggagta ggaggacccg gccataaggc aagagttttg   1200
gctgaagcaa tgagccaagt aacaaataca gctaccataa tgatgcagag aggcaatttt   1260
aggaaccaaa gaaagatggt taagtgtttc aattgtggca agaagggca cacagccaga   1320 aattgcaggg cccctaggaa aaagggctgt tggaaatgtg gaaaggaagg acaccaaatg   1380
aaagattgta ctgagagaca ggctaatttt ttagggaaga tctggccttc ctacaaggga   1440
aggccaggga attttcttca gagcagacca gagccaacag ccccaccatt tcttcagagc   1500
agaccagagc caacagcccc accagaagag agcttcaggt ctgggtagga gacaacaact   1560
ccccctcaga agcaggagcc gatagacaag gaactgtatc ctttaacttc cctcagatca   1620
ctctttggca acgacccctc gtcacaataa agatagggg gcaactaaag gaagctctat   1680
tagatacagg agcagatgat acagtattag aagaaatgag tttgccagga agatggaaac   1740
caaaaatgat agggggaatt ggaggtttta tcaaagtaag acagtatgat cagatactca   1800
tagaaatctg tggacataaa gctataggta cagtattagt aggacctaca cctgtcaaca   1860
taattggaag aaatctgttg actcagattg gttgcacttt aaattttccc attagccta   1920 ttgagactgt accagtaaaa ttaaagccag gaatggatgg cccaaaagtt aaacaatggc   1980
cattgacaga agaaaaaata aaagcattag tagaaatttg tacagaaatg gaaaaggaag   2040
ggaaaatttc aaaaattggg cctgagaatc catacaatac tccagtatt gccataaaga   2100 aaaaagacag tactaaatgg agaaaattag tagatttcag agaacttaat aagagaactc   2160
aagacttctg ggaagttcaa ttaggaatac cacatcccgc agggttaaaa aagaaaaat   2220 cagtaacagt actggatgtg ggtgatgcat atttttcagt tcccttagat gaagacttca   2280
ggaagtatac tgcatttacc atacctagta taaacaatga gacaccaggg attagatatc   2340
agtacaatgt gcttccacag ggatggaaag gatcaccagc aatattccaa agtagcatga   2400
caaaaatctt agagcctttt aaaaaacaaa atccagacat agttatctat caatacatgg   2460
atgatttgta tgtaggatct gacttagaaa tagggcagca tagaacaaaa atagaggagc   2520
tgagacaaca tctgttgagg tggggactta ccacaccaga caaaaaacat cagaaagaac   2580
ctccattcct ttggatgggt tatgaactcc atcctgataa atggacagta cagcctatag   2640
tgctgccaga aaaagacagc tggactgtca atgcatacaa gaagttagtg gggaaattga   2700
attgggcaag tcagatttac ccagggatta agtaaggca attatgtaaa ctccttagag   2760
gaaccaaagc actaacagaa gtaataccac taacagaaga agcagagcta gaactggcag   2820
aaaacagaga gattctaaaa gaaccagtac atggagtgta ttatgaccca tcaaaagact   2880
taatagcaga aatacagaag caggggcaag gccaatggac atatcaaatt tatcaagagc   2940
catttaaaaa tctgaaaaca ggaaaatatg caagaatgag gggtgcccac actaatgatg   3000
taaaacaatt aacagaggca gtgcaaaaaa taaccacaga aagcatagta atatggggaa   3060
agactcctaa atttaaacta cccatacaaa aggaaacatg gaaacatgg tggacagagt   3120 attggcaagc cacctggatt cctgagtggg agtttgttaa tacccctcct ttagtgaaat   3180
tatggtacca gttagagaaa gaacccatag taggagcaga aaccttctat gtagatgggg   3240
```

```
cagctaacag ggagactaaa ttaggaaaag caggatatgt tactaacaaa ggaagacaaa   3300
aggttgtccc cctaactaac acaacaaatc agaaaactga gttacaagca atttatctag   3360
ctttgcagga ttcaggatta gaagtaaaca tagtaacaga ctcacaatat gcattaggaa   3420
tcattcaagc acaaccagat aaagtgaatc agagttagt  caatcaaata atagagcagt   3480
taataaaaaa ggaaaaggtc tatctggcat gggtaccagc acacaaagga attggaggaa   3540
atgaacaagt agataaatta gtcagtgctg gaatcaggaa aatactattt ttagatggaa   3600
tagataaggc ccaagatgaa catgagaaat atcacagtaa ttggagagca atggctagtg   3660
attttaacct gccacctgta gtagcaaaag aaatagtagc cagctgtgat aaatgtcagc   3720
taaaaggaga agccatgcat ggacaagtag actgtagtcc aggaatatgg caactagatt   3780
gtacacattt agaaggaaaa gttatcctgg tagcagttca tgtagccagt ggatatatag   3840
aagcagaagt tattccagca gaaacagggc aggaaacagc atattttctt ttaaaattag   3900
caggaagatg gccagtaaaa acaatacata cagacaatgg cagcaatttc accagtgcta   3960
cggttaaggc cgcctgttgg tgggcgggaa tcaagcagga atttggaatt ccctacaatc   4020
cccaaagtca aggagtagta gaatctatga ataaagaatt aaagaaaatt ataggacagg   4080
taagagatca ggctgaacat cttaagacag cagtacaaat ggcagtattc atccacaatt   4140
ttaaaagaaa agggggggatt ggggggtaca gtgcagggga agaatagta gacataatag   4200 caacagacat acaaactaaa gaattacaaa aacaaattac aaaaattcaa aattttcggg   4260
tttattacag ggacagcaga atccactttg gaaaggacca gcaaagctc  ctctggaaag   4320 gtgaaggggc agtagtaata caagataata gtgacataaa agtagtgcca agaagaaaag   4380
caaagatcat tagggattat ggaaaacaga tggcaggtga tgattgtgtg gcaagtagac   4440
aggatgagga ttagaacatg gaaaagttta gtaaaacacc atatgtatgt ttcagggaaa   4500
gctaggggat ggttttatag acatcactat gaaagccctc atccaagaat aagttcagaa   4560
gtacacatcc cactagggga tgctagattg gtaataacaa catattgggg tctgcataca   4620
ggagaaagag actggcattt gggtcaggga gtctccatag aatggaggaa aaagagatat   4680
agcacacaag tagaccctga actagcagac caactaattc atctgtatta ctttgactgt   4740
ttttcagact ctgctataag aaaggcctta ttaggacaca tagttagccc taggtgtgaa   4800
tatcaagcag gacataacaa ggtaggatct ctacaatact tggcactagc agcattaata   4860
acaccaaaaa agataaagcc acctttgcct agtgttacga aactgacaga ggatagatgg   4920
aacaagcccc agaagaccaa gggccacaga gggagccaca caatgaatgg acactagagc   4980
ttttagagga gcttaagaat gaagctgtta gacattttcc taggatttgg ctccatggct   5040
tagggcaaca tatctatgaa acttatgggg atacttgggc aggagtggaa gccataataa   5100
gaattctgca acaactgctg tttatccatt ttcagaattg ggtgtcgaca tagcagaata   5160
ggcgttactc gacagaggag agcaagaaat ggagccagta gatcctagac tagagccctg   5220
gaagcatcca ggaagtcagc ctaaaactgc ttgtaccaat tgctattgta aaaagtgttg   5280
ctttcattgc caagtttgtt tcataacaaa agccttaggc atctcctatg gcaggaagaa   5340
gcggagacag cgacgaagac ctcctcaagg cagtcagact catcaagttt ctctatcaaa   5400
gcagtaagta gtacatgtaa tgcaacctat acaaatagca atagtagcat tagtagtagc   5460
aataataata gcaatagttg tgtggtccat agtaatcata gaatatagga aaatattaag   5520
acaaagaaaa atagacaggt taattgatag actaatagaa agagcagaag acagtggcaa   5580
tgagagtgaa ggagaaatat cagcacttgt ggagatgggg gtggagatgg ggcaccatgc   5640
```

```
tccttgggat gttgatgatc tgtagtgcta cagaaaaatt gtgggtcaca gtctattatg    5700
gggtacctgt gtggaaggaa gcaaccacca ctctattttg tgcatcagat gctaaagcat    5760
atgatacaga ggtacataat gtttgggcca cacatgcctg tgtacccaca gaccccaacc    5820
cacaagaagt agtattggta aatgtgacag aaaattttaa catgtggaaa atgacatgg     5880 tagaacagat gcatgaggat ataatcagtt tatgggatca aagcctaaag ccatgtgtaa    5940
aattaacccc actctgtgtt agtttaaagt gcactgattt gaagaatgat actaatacca    6000
atagtagtag cgggagaatg ataatggaga aggagagat aaaaaactgc tctttcaata    6060
tcagcacaag cataagaggt aaggtgcaga agaatatgc attttttat aaacttgata     6120 taataccaat agataatgat actaccagct atacgttgac aagttgtaac acctcagtca    6180
ttacacaggc ctgtccaaag gtatcctttg agccaattcc catacattat tgtgccccgg    6240
ctggttttgc gattctaaaa tgtaataata agacgttcaa tggaacagga ccatgtacaa    6300
atgtcagcac agtacaatgt acacatggaa ttaggccagt agtatcaact caactgctgt    6360
taaatggcag tctggcagaa gaagaggtag taattagatc tgccaatttc acagacaatg    6420
ctaaaaccat aatagtacag ctgaaccaat ctgtagaaat taattgtaca agacccaaca    6480
acaatacaag aaaaagtatc cgtatccaga gaggaccagg gagagcattt gttacaatag    6540
gaaaaatagg aaatatgaga caagcacatt gtaacattag tagagcaaaa tggaataaca    6600
ctttaaaaca gatagatagc aaattaagag aacaatttgg aaataataaa acaataatct    6660
ttaagcagtc ctcaggaggg gacccagaaa ttgtaacgca cagttttaat tgtggagggg    6720 aattttcta ctgtaattca acacaactgt taatagtac ttggtttaat agtacttgga    6780
gtactaaagg gtcaaataac actgaaggaa gtgacacaat caccctccca tgcagaataa    6840
aacaaattat aaacatgtgg caggaagtag aaaagcaat gtatgcccct cccatcagtg    6900
gacaaattag atgttcatca aatattacag ggctgctatt aacaagagat ggtggtaata    6960
gcaacaatga gtccgagatc ttcagacctg gaggaggaga tatgagggac aattggagaa    7020
gtgaattata taaatataaa gtagtaaaaa ttgaaccatt aggagtagca cccaccaagg    7080
caaagagaag agtggtgcag agagaaaaaa gagcagtggg aataggagct ttgttccttg    7140
ggttcttggg agcagcagga agcactatgg gcgcagcgtc aatgacgctg acggtacagg    7200
ccagacaatt attgtctggt atagtgcagc agcagaacaa tttgctgagg gctattgagg    7260
cgcaacagca tctgttgcaa ctcacagtct ggggcatcaa gcagctccag gcaagaatcc    7320
tggctgtgga agataccta aaggatcaac agctcctggg gatttggggt tgctctggaa    7380
aactcatttg caccactgct gtgccttgga atgctagttg gagtaataaa tctctggaac    7440
agatttggaa taacatgacc tggatggagt gggacagaga aattaacaat tacacaagct    7500
taatacactc cttaattgaa gaatcgcaaa accagcaaga aaagaatgaa caagaattat    7560
tggaattaga taaatgggca agtttgtgga attggtttaa cataacaaat tggctgtggt    7620
atataaaatt attcataatg atagtaggag gcttggtagg tttaagaata gttttgctg    7680 tactttctgt agtgaataga gttaggcagg gatattcacc attatcgttt cagacccacc    7740
tcccaatccc gagggaccc gacaggcccg aaggaataga agaagaaggt ggagagagag    7800
acagagacag atccattcga ttagtgaacg gatccttagc acttatctgg gacgatctgc    7860
ggagcctgtg cctcttcagc taccaccgct tgagagactt actcttgatt gtaacgagga    7920
ttgtggaact tctgggacgc agggggtggg aagcccctcaa atattggtgg aatctcctac    7980
```

-continued

```
agtattggag tcaggagcta aagaatagtg ctgttagctt gctcaatgcc acagctatag    8040
cagtagctga ggggacagat agggttatag aagtagtaca aggagcttat agagctattc    8100
gccacatacc tagaagaata agacagggct tggaaaggat tttgctataa gatgggtggc    8160
aagtggtcaa aaagtagtgt ggttggatgg cctgctgtaa gggaaagaat gagacgagct    8220
gagccagcag cagatgggt gggagcagca tctcgagacc tagaaaaaca tggagcaatc    8280
acaagtagca acacagcagc taacaatgct gattgtgcct ggctagaagc acaagaggag    8340
gaggaggtgg gttttccagt cacacctcag gtacctttaa gaccaatgac ttacaaggca    8400
gctgtagatc ttagccactt tttaaaagaa aagggggac tggaagggct aattcactcc    8460
caacgaagac aagatatcct tgatctgtgg atctaccaca caaggcta cttccctgat     8520 tagcagaact acacaccagg gccagggatc agatatccac tgacctttgg atggtgctac    8580
aagctagtac cagttgagcc agagaagtta gaagaagcca acaaaggaga gaacaccagc    8640
ttgttacacc ctgtgagcct gcatggaatg gatgacccgg agagagaagt gttagagtgg    8700
aggtttgaca gccgcctagc atttcatcac atggcccgag agctgcatcc ggagtacttc    8760
aagaactgct gacatcgagc ttgctacaag ggactttccg ctggggactt tccagggagg    8820
cgtggcctgg gcgggactgg ggagtggcga gccctcagat cctgcatata agcagctgct    8880
ttttgcctgt actgggtctc tctggttaga ccagatctga gcctgggagc tc            8932
```

<210> SEQ ID NO 2
<211> LENGTH: 512
<212> TYPE: PRT
<213> ORGANISM: Human imunodeficiency virus type 1

<400> SEQUENCE: 2

```
Met Gly Ala Arg Ala Ser Val Leu Ser Gly Gly Glu Leu Asp Arg Trp
1               5                   10                  15

Glu Lys Ile Arg Leu Arg Pro Gly Gly Lys Lys Tyr Lys Leu Lys
            20                  25                  30

His Ile Val Trp Ala Ser Arg Glu Leu Glu Arg Phe Ala Val Asn Pro
        35                  40                  45

Gly Leu Leu Glu Thr Ser Glu Gly Cys Arg Gln Ile Leu Gly Gln Leu
    50                  55                  60

Gln Pro Ser Leu Gln Thr Gly Ser Glu Glu Leu Arg Ser Leu Tyr Asn
65                  70                  75                  80

Thr Val Ala Thr Leu Tyr Cys Val His Gln Arg Ile Glu Ile Lys Asp
                85                  90                  95

Thr Lys Glu Ala Leu Asp Lys Ile Glu Glu Glu Gln Asn Lys Ser Lys
            100                 105                 110

Lys Lys Ala Gln Gln Ala Ala Ala Asp Thr Gly His Ser Ser Gln Val
        115                 120                 125

Ser Gln Asn Tyr Pro Ile Val Gln Asn Ile Gln Gly Gln Met Val His
    130                 135                 140

Gln Ala Ile Ser Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Thr Met Leu Asn Thr Val Gly
            180                 185                 190

Gly His Gln Ala Ala Met Gln Met Leu Lys Glu Thr Ile Asn Glu Glu
        195                 200                 205
```

```
Ala Ala Glu Trp Asp Arg Val His Pro Val His Ala Gly Pro Ile Ala
    210                 215                 220

Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr Asn Asn Pro Pro Ile
                245                 250                 255

Pro Val Gly Glu Ile Tyr Lys Arg Trp Ile Ile Leu Gly Leu Asn Lys
            260                 265                 270

Ile Val Arg Met Tyr Ser Pro Thr Ser Ile Leu Asp Ile Arg Gln Gly
        275                 280                 285

Pro Lys Glu Pro Phe Arg Asp Tyr Val Asp Arg Phe Tyr Lys Thr Leu
    290                 295                 300

Arg Ala Glu Gln Ala Ser Gln Glu Val Lys Asn Trp Met Thr Glu Thr
305                 310                 315                 320

Leu Leu Val Gln Asn Ala Asn Pro Asp Cys Lys Thr Ile Leu Lys Ala
                325                 330                 335

Leu Gly Pro Ala Ala Thr Leu Glu Glu Met Met Thr Ala Cys Gln Gly
            340                 345                 350

Val Gly Gly Pro Gly His Lys Ala Arg Val Leu Ala Glu Ala Met Ser
        355                 360                 365

Gln Val Thr Asn Thr Ala Thr Ile Met Met Gln Arg Gly Asn Phe Arg
    370                 375                 380

Asn Gln Arg Lys Met Val Lys Cys Phe Asn Cys Gly Lys Glu Gly His
385                 390                 395                 400

Thr Ala Arg Asn Cys Arg Ala Pro Arg Lys Lys Gly Cys Trp Lys Cys
                405                 410                 415

Gly Lys Glu Gly His Gln Met Lys Asp Cys Thr Glu Arg Gln Ala Asn
            420                 425                 430

Phe Leu Gly Lys Ile Trp Pro Ser Tyr Lys Gly Arg Pro Gly Asn Phe
        435                 440                 445

Leu Gln Ser Arg Pro Glu Pro Thr Ala Pro Pro Phe Leu Gln Ser Arg
    450                 455                 460

Pro Glu Pro Thr Ala Pro Pro Glu Glu Ser Phe Arg Ser Gly Val Glu
465                 470                 475                 480

Thr Thr Thr Pro Pro Gln Lys Gln Glu Pro Ile Asp Lys Glu Leu Tyr
                485                 490                 495

Pro Leu Thr Ser Leu Arg Ser Leu Phe Gly Asn Asp Pro Ser Ser Gln
            500                 505                 510

<210> SEQ ID NO 3
<211> LENGTH: 1015
<212> TYPE: PRT
<213> ORGANISM: Human imunodeficiency virus type 1

<400> SEQUENCE: 3

Phe Phe Arg Glu Asp Leu Ala Phe Leu Gln Gly Lys Ala Arg Glu Phe
1               5                   10                  15

Ser Ser Glu Gln Thr Arg Ala Asn Ser Pro Thr Ile Ser Ser Glu Gln
            20                  25                  30

Thr Arg Ala Asn Ser Pro Thr Arg Arg Glu Leu Gln Val Trp Gly Arg
        35                  40                  45

Asp Asn Asn Ser Pro Ser Glu Ala Gly Ala Asp Arg Gln Gly Thr Val
    50                  55                  60

Ser Phe Asn Phe Pro Gln Ile Thr Leu Trp Gln Arg Pro Leu Val Thr
65                  70                  75                  80
```

-continued

```
Ile Lys Ile Gly Gly Gln Leu Lys Glu Ala Leu Leu Asp Thr Gly Ala
                 85                  90                  95
Asp Asp Thr Val Leu Glu Glu Met Ser Leu Pro Gly Arg Trp Lys Pro
            100                 105                 110
Lys Met Ile Gly Gly Ile Gly Gly Phe Ile Lys Val Arg Gln Tyr Asp
        115                 120                 125
Gln Ile Leu Ile Glu Ile Cys Gly His Lys Ala Ile Gly Thr Val Leu
    130                 135                 140
Val Gly Pro Thr Pro Val Asn Ile Ile Gly Arg Asn Leu Leu Thr Gln
145                 150                 155                 160
Ile Gly Cys Thr Leu Asn Phe Pro Ile Ser Pro Ile Glu Thr Val Pro
                165                 170                 175
Val Lys Leu Lys Pro Gly Met Asp Gly Pro Lys Val Lys Gln Trp Pro
            180                 185                 190
Leu Thr Glu Glu Lys Ile Lys Ala Leu Val Glu Ile Cys Thr Glu Met
        195                 200                 205
Glu Lys Glu Gly Lys Ile Ser Lys Ile Gly Pro Glu Asn Pro Tyr Asn
    210                 215                 220
Thr Pro Val Phe Ala Ile Lys Lys Asp Ser Thr Lys Trp Arg Lys
225                 230                 235                 240
Leu Val Asp Phe Arg Glu Leu Asn Lys Arg Thr Gln Asp Phe Trp Glu
                245                 250                 255
Val Gln Leu Gly Ile Pro His Pro Ala Gly Leu Lys Lys Lys Lys Ser
            260                 265                 270
Val Thr Val Leu Asp Val Gly Asp Ala Tyr Phe Ser Val Pro Leu Asp
        275                 280                 285
Glu Asp Phe Arg Lys Tyr Thr Ala Phe Thr Ile Pro Ser Ile Asn Asn
    290                 295                 300
Glu Thr Pro Gly Ile Arg Tyr Gln Tyr Asn Val Leu Pro Gln Gly Trp
305                 310                 315                 320
Lys Gly Ser Pro Ala Ile Phe Gln Ser Ser Met Thr Lys Ile Leu Glu
                325                 330                 335
Pro Phe Lys Lys Gln Asn Pro Asp Ile Val Ile Tyr Gln Tyr Met Asp
            340                 345                 350
Asp Leu Tyr Val Gly Ser Asp Leu Glu Ile Gly Gln His Arg Thr Lys
        355                 360                 365
Ile Glu Glu Leu Arg Gln His Leu Leu Arg Trp Gly Leu Thr Thr Pro
    370                 375                 380
Asp Lys Lys His Gln Lys Glu Pro Pro Phe Leu Trp Met Gly Tyr Glu
385                 390                 395                 400
Leu His Pro Asp Lys Trp Thr Val Gln Pro Ile Val Leu Pro Glu Lys
                405                 410                 415
Asp Ser Trp Thr Val Asn Asp Ile Gln Lys Leu Val Gly Lys Leu Asn
            420                 425                 430
Trp Ala Ser Gln Ile Tyr Pro Gly Ile Lys Val Arg Gln Leu Cys Lys
        435                 440                 445
Leu Leu Arg Gly Thr Lys Ala Leu Thr Glu Val Ile Pro Leu Thr Glu
    450                 455                 460
Glu Ala Glu Leu Glu Leu Ala Glu Asn Arg Glu Ile Leu Lys Glu Pro
465                 470                 475                 480
Val His Gly Val Tyr Tyr Asp Pro Ser Lys Asp Leu Ile Ala Glu Ile
                485                 490                 495
```

-continued

```
Gln Lys Gln Gly Gln Gly Gln Trp Thr Tyr Gln Ile Tyr Gln Glu Pro
            500                 505                 510

Phe Lys Asn Leu Lys Thr Gly Lys Tyr Ala Arg Met Arg Gly Ala His
            515                 520                 525

Thr Asn Asp Val Lys Gln Leu Thr Glu Ala Val Gln Lys Ile Thr Thr
            530                 535                 540

Glu Ser Ile Val Ile Trp Gly Lys Thr Pro Lys Phe Lys Leu Pro Ile
545                 550                 555                 560

Gln Lys Glu Thr Trp Glu Thr Trp Trp Thr Glu Tyr Trp Gln Ala Thr
                565                 570                 575

Trp Ile Pro Glu Trp Glu Phe Val Asn Thr Pro Leu Val Lys Leu
                580                 585                 590

Trp Tyr Gln Leu Glu Lys Glu Pro Ile Val Gly Ala Glu Thr Phe Tyr
                595                 600                 605

Val Asp Gly Ala Ala Asn Arg Glu Thr Lys Leu Gly Lys Ala Gly Tyr
            610                 615                 620

Val Thr Asn Lys Gly Arg Gln Lys Val Val Pro Leu Thr Asn Thr Thr
625                 630                 635                 640

Asn Gln Lys Thr Glu Leu Gln Ala Ile Tyr Leu Ala Leu Gln Asp Ser
                645                 650                 655

Gly Leu Glu Val Asn Ile Val Thr Asp Ser Gln Tyr Ala Leu Gly Ile
            660                 665                 670

Ile Gln Ala Gln Pro Asp Lys Ser Glu Ser Glu Leu Val Asn Gln Ile
        675                 680                 685

Ile Glu Gln Leu Ile Lys Lys Glu Lys Val Tyr Leu Ala Trp Val Pro
    690                 695                 700

Ala His Lys Gly Ile Gly Gly Asn Glu Gln Val Asp Lys Leu Val Ser
705                 710                 715                 720

Ala Gly Ile Arg Lys Ile Leu Phe Leu Asp Gly Ile Asp Lys Ala Gln
                725                 730                 735

Asp Glu His Glu Lys Tyr His Ser Asn Trp Arg Ala Met Ala Ser Asp
            740                 745                 750

Phe Asn Leu Pro Pro Val Val Ala Lys Glu Ile Val Ala Ser Cys Asp
            755                 760                 765

Lys Cys Gln Leu Lys Gly Glu Ala Met His Gly Gln Val Asp Cys Ser
770                 775                 780

Pro Gly Ile Trp Gln Leu Asp Cys Thr His Leu Glu Gly Lys Val Ile
785                 790                 795                 800

Leu Val Ala Val His Val Ala Ser Gly Tyr Ile Glu Ala Glu Val Ile
                805                 810                 815

Pro Ala Glu Thr Gly Gln Glu Thr Ala Tyr Phe Leu Leu Lys Leu Ala
            820                 825                 830

Gly Arg Trp Pro Val Lys Thr Ile His Thr Asp Asn Gly Ser Asn Phe
            835                 840                 845

Thr Ser Ala Thr Val Lys Ala Ala Cys Trp Trp Ala Gly Ile Lys Gln
            850                 855                 860

Glu Phe Gly Ile Pro Tyr Asn Pro Gln Ser Gln Gly Val Val Glu Ser
865                 870                 875                 880

Met Asn Lys Glu Leu Lys Lys Ile Ile Gly Gln Val Arg Asp Gln Ala
                885                 890                 895

Glu His Leu Lys Thr Ala Val Gln Met Ala Val Phe Ile His Asn Phe
            900                 905                 910
```

-continued

```
Lys Arg Lys Gly Gly Ile Gly Gly Tyr Ser Ala Gly Glu Arg Ile Val
        915                 920                 925

Asp Ile Ile Ala Thr Asp Ile Gln Thr Lys Glu Leu Gln Lys Gln Ile
        930                 935                 940

Thr Lys Ile Gln Asn Phe Arg Val Tyr Tyr Arg Asp Ser Arg Asn Pro
945                 950                 955                 960

Leu Trp Lys Gly Pro Ala Lys Leu Leu Trp Lys Gly Glu Gly Ala Val
                965                 970                 975

Val Ile Gln Asp Asn Ser Asp Ile Lys Val Val Pro Arg Arg Lys Ala
                980                 985                 990

Lys Ile Ile Arg Asp Tyr Gly Lys  Gln Met Ala Gly Asp  Asp Cys Val
        995                 1000                1005

Ala Ser  Arg Gln Asp Glu Asp
    1010                1015

<210> SEQ ID NO 4
<211> LENGTH: 192
<212> TYPE: PRT
<213> ORGANISM: Human imunodeficiency virus type 1

<400> SEQUENCE: 4

Met Glu Asn Arg Trp Gln Val Met Ile Val Trp Gln Val Asp Arg Met
1               5                   10                  15

Arg Ile Arg Thr Trp Lys Ser Leu Val Lys His His Met Tyr Val Ser
                20                  25                  30

Gly Lys Ala Arg Gly Trp Phe Tyr Arg His His Tyr Glu Ser Pro His
            35                  40                  45

Pro Arg Ile Ser Ser Glu Val His Ile Pro Leu Gly Asp Ala Arg Leu
        50                  55                  60

Val Ile Thr Thr Tyr Trp Gly Leu His Thr Gly Glu Arg Asp Trp His
65                  70                  75                  80

Leu Gly Gln Gly Val Ser Ile Glu Trp Arg Lys Lys Arg Tyr Ser Thr
                85                  90                  95

Gln Val Asp Pro Glu Leu Ala Asp Gln Leu Ile His Leu Tyr Tyr Phe
                100                 105                 110

Asp Cys Phe Ser Asp Ser Ala Ile Arg Lys Ala Leu Leu Gly His Ile
            115                 120                 125

Val Ser Pro Arg Cys Glu Tyr Gln Ala Gly His Asn Lys Val Gly Ser
        130                 135                 140

Leu Gln Tyr Leu Ala Leu Ala Ala Leu Ile Thr Pro Lys Lys Ile Lys
145                 150                 155                 160

Pro Pro Leu Pro Ser Val Thr Lys Leu Thr Glu Asp Arg Trp Asn Lys
                165                 170                 175

Pro Gln Lys Thr Lys Gly His Arg Gly Ser His Thr Met Asn Gly His
                180                 185                 190

<210> SEQ ID NO 5
<211> LENGTH: 78
<212> TYPE: PRT
<213> ORGANISM: Human imunodeficiency virus type 1

<400> SEQUENCE: 5

Met Glu Gln Ala Pro Glu Asp Gln Gly Pro Gln Arg Glu Pro His Asn
1               5                   10                  15

Glu Trp Thr Leu Glu Leu Leu Glu Glu Leu Lys Asn Glu Ala Val Arg
                20                  25                  30
```

-continued

```
His Phe Pro Arg Ile Trp Leu His Gly Leu Gly Gln His Ile Tyr Glu
            35                  40                  45

Thr Tyr Gly Asp Thr Trp Ala Gly Val Glu Ala Ile Ile Arg Ile Leu
        50                  55                  60

Gln Gln Leu Leu Phe Ile His Phe Gln Asn Trp Val Ser Thr
65                  70                  75
```

<210> SEQ ID NO 6
<211> LENGTH: 86
<212> TYPE: PRT
<213> ORGANISM: Human imunodeficiency virus type 1

<400> SEQUENCE: 6

```
Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Cys Phe
            20                  25                  30

His Cys Gln Val Cys Phe Ile Thr Lys Ala Leu Gly Ile Ser Tyr Gly
        35                  40                  45

Arg Lys Lys Arg Arg Gln Arg Arg Pro Pro Gln Gly Ser Gln Thr
    50                  55                  60

His Gln Val Ser Leu Ser Lys Gln Pro Thr Ser Gln Ser Arg Gly Asp
65                  70                  75                  80

Pro Thr Gly Pro Lys Glu
                85
```

<210> SEQ ID NO 7
<211> LENGTH: 116
<212> TYPE: PRT
<213> ORGANISM: Human imunodeficiency virus type 1

<400> SEQUENCE: 7

```
Met Ala Gly Arg Ser Gly Asp Ser Asp Glu Asp Leu Leu Lys Ala Val
1               5                   10                  15

Arg Leu Ile Lys Phe Leu Tyr Gln Ser Asn Pro Pro Asn Pro Glu
            20                  25                  30

Gly Thr Arg Gln Ala Arg Arg Asn Arg Arg Arg Trp Arg Glu Arg
        35                  40                  45

Gln Arg Gln Ile His Ser Ile Ser Glu Arg Ile Leu Ser Thr Tyr Leu
    50                  55                  60

Gly Arg Ser Ala Glu Pro Val Pro Leu Gln Leu Pro Pro Leu Glu Arg
65                  70                  75                  80

Leu Thr Leu Asp Cys Asn Glu Asp Cys Gly Thr Ser Gly Thr Gln Gly
                85                  90                  95

Val Gly Ser Pro Gln Ile Leu Val Glu Ser Pro Thr Val Leu Glu Ser
            100                 105                 110

Gly Ala Lys Glu
        115
```

<210> SEQ ID NO 8
<211> LENGTH: 81
<212> TYPE: PRT
<213> ORGANISM: Human imunodeficiency virus type 1

<400> SEQUENCE: 8

```
Met Gln Pro Ile Gln Ile Ala Ile Val Ala Leu Val Val Ala Ile Ile
1               5                   10                  15
```

```
Ile Ala Ile Val Val Trp Ser Ile Val Ile Glu Tyr Arg Lys Ile
                20                  25                  30

Leu Arg Gln Arg Lys Ile Asp Arg Leu Ile Asp Arg Leu Ile Glu Arg
            35                  40                  45

Ala Glu Asp Ser Gly Asn Glu Ser Glu Gly Glu Ile Ser Ala Leu Val
 50                  55                  60

Glu Met Gly Val Glu Met Gly His His Ala Pro Trp Asp Val Asp Asp
 65                  70                  75                  80

Leu

<210> SEQ ID NO 9
<211> LENGTH: 856
<212> TYPE: PRT
<213> ORGANISM: Human imunodeficiency virus type 1
<220> FEATURE:
<221> NAME/KEY: PEPTIDE
<222> LOCATION: (79)..(184)
<221> NAME/KEY: PEPTIDE
<222> LOCATION: (326)..(400)

<400> SEQUENCE: 9

Met Arg Val Lys Glu Lys Tyr Gln His Leu Trp Arg Trp Gly Trp Arg
 1               5                  10                  15

Trp Gly Thr Met Leu Leu Gly Met Leu Met Ile Cys Ser Ala Thr Glu
                20                  25                  30

Lys Leu Trp Val Thr Val Tyr Tyr Gly Val Pro Val Trp Lys Glu Ala
            35                  40                  45

Thr Thr Thr Leu Phe Cys Ala Ser Asp Ala Lys Ala Tyr Asp Thr Glu
 50                  55                  60

Val His Asn Val Trp Ala Thr His Ala Cys Val Pro Thr Asp Pro Asn
 65                  70                  75                  80

Pro Gln Glu Val Val Leu Val Asn Val Thr Glu Asn Phe Asn Met Trp
                85                  90                  95

Lys Asn Asp Met Val Glu Gln Met His Glu Asp Ile Ile Ser Leu Trp
            100                 105                 110

Asp Gln Ser Leu Lys Pro Cys Val Lys Leu Thr Pro Leu Cys Val Ser
        115                 120                 125

Leu Lys Cys Thr Asp Leu Lys Asn Asp Thr Asn Thr Asn Ser Ser Ser
130                 135                 140

Gly Arg Met Ile Met Glu Lys Gly Glu Ile Lys Asn Cys Ser Phe Asn
145                 150                 155                 160

Ile Ser Thr Ser Ile Arg Gly Lys Val Gln Lys Glu Tyr Ala Phe Phe
                165                 170                 175

Tyr Lys Leu Asp Ile Ile Pro Ile Asp Asn Asp Thr Thr Ser Tyr Thr
            180                 185                 190

Leu Thr Ser Cys Asn Thr Ser Val Ile Thr Gln Ala Cys Pro Lys Val
        195                 200                 205

Ser Phe Glu Pro Ile Pro Ile His Tyr Cys Ala Pro Ala Gly Phe Ala
210                 215                 220

Ile Leu Lys Cys Asn Asn Lys Thr Phe Asn Gly Thr Gly Pro Cys Thr
225                 230                 235                 240

Asn Val Ser Thr Val Gln Cys Thr His Gly Ile Arg Pro Val Val Ser
                245                 250                 255

Thr Gln Leu Leu Leu Asn Gly Ser Leu Ala Glu Glu Val Val Ile
            260                 265                 270
```

-continued

```
Arg Ser Ala Asn Phe Thr Asp Asn Ala Lys Thr Ile Ile Val Gln Leu
        275                 280                 285

Asn Gln Ser Val Glu Ile Asn Cys Thr Arg Pro Asn Asn Asn Thr Arg
    290                 295                 300

Lys Ser Ile Arg Ile Gln Arg Gly Pro Gly Arg Ala Phe Val Thr Ile
305                 310                 315                 320

Gly Lys Ile Gly Asn Met Arg Gln Ala His Cys Asn Ile Ser Arg Ala
                325                 330                 335

Lys Trp Asn Asn Thr Leu Lys Gln Ile Asp Ser Lys Leu Arg Glu Gln
            340                 345                 350

Phe Gly Asn Asn Lys Thr Ile Ile Phe Lys Gln Ser Ser Gly Gly Asp
        355                 360                 365

Pro Glu Ile Val Thr His Ser Phe Asn Cys Gly Gly Glu Phe Phe Tyr
    370                 375                 380

Cys Asn Ser Thr Gln Leu Phe Asn Ser Thr Trp Phe Asn Ser Thr Trp
385                 390                 395                 400

Ser Thr Lys Gly Ser Asn Asn Thr Glu Gly Ser Asp Thr Ile Thr Leu
                405                 410                 415

Pro Cys Arg Ile Lys Gln Ile Ile Asn Met Trp Gln Glu Val Gly Lys
            420                 425                 430

Ala Met Tyr Ala Pro Pro Ile Ser Gly Gln Ile Arg Cys Ser Ser Asn
        435                 440                 445

Ile Thr Gly Leu Leu Leu Thr Arg Asp Gly Gly Asn Ser Asn Asn Glu
    450                 455                 460

Ser Glu Ile Phe Arg Pro Gly Gly Gly Asp Met Arg Asp Asn Trp Arg
465                 470                 475                 480

Ser Glu Leu Tyr Lys Tyr Lys Val Val Lys Ile Glu Pro Leu Gly Val
                485                 490                 495

Ala Pro Thr Lys Ala Lys Arg Arg Val Val Gln Arg Glu Lys Arg Ala
            500                 505                 510

Val Gly Ile Gly Ala Leu Phe Leu Gly Phe Leu Gly Ala Ala Gly Ser
        515                 520                 525

Thr Met Gly Ala Ala Ser Met Thr Leu Thr Val Gln Ala Arg Gln Leu
    530                 535                 540

Leu Ser Gly Ile Val Gln Gln Gln Asn Asn Leu Leu Arg Ala Ile Glu
545                 550                 555                 560

Ala Gln Gln His Leu Leu Gln Leu Thr Val Trp Gly Ile Lys Gln Leu
                565                 570                 575

Gln Ala Arg Ile Leu Ala Val Glu Arg Tyr Leu Lys Asp Gln Gln Leu
            580                 585                 590

Leu Gly Ile Trp Gly Cys Ser Gly Lys Leu Ile Cys Thr Thr Ala Val
        595                 600                 605

Pro Trp Asn Ala Ser Trp Ser Asn Lys Ser Leu Glu Gln Ile Trp Asn
    610                 615                 620

Asn Met Thr Trp Met Glu Trp Asp Arg Glu Ile Asn Asn Tyr Thr Ser
625                 630                 635                 640

Leu Ile His Ser Leu Ile Glu Glu Ser Gln Asn Gln Gln Glu Lys Asn
                645                 650                 655

Glu Gln Glu Leu Leu Glu Leu Asp Lys Trp Ala Ser Leu Trp Asn Trp
            660                 665                 670

Phe Asn Ile Thr Asn Trp Leu Trp Tyr Ile Lys Leu Phe Ile Met Ile
        675                 680                 685
```

```
Val Gly Gly Leu Val Gly Leu Arg Ile Val Phe Ala Val Leu Ser Val
    690                 695                 700
Val Asn Arg Val Arg Gln Gly Tyr Ser Pro Leu Ser Phe Gln Thr His
705                 710                 715                 720
Leu Pro Ile Pro Arg Gly Pro Asp Arg Pro Glu Gly Ile Glu Glu Glu
                725                 730                 735
Gly Gly Glu Arg Asp Arg Asp Ser Ile Arg Leu Val Asn Gly Ser
                740                 745                 750
Leu Ala Leu Ile Trp Asp Asp Leu Arg Ser Leu Cys Leu Phe Ser Tyr
            755                 760                 765
His Arg Leu Arg Asp Leu Leu Leu Ile Val Thr Arg Ile Val Glu Leu
        770                 775                 780
Leu Gly Arg Arg Gly Trp Glu Ala Leu Lys Tyr Trp Trp Asn Leu Leu
785                 790                 795                 800
Gln Tyr Trp Ser Gln Glu Leu Lys Asn Ser Ala Val Ser Leu Leu Asn
                805                 810                 815
Ala Thr Ala Ile Ala Val Ala Glu Gly Thr Asp Arg Val Ile Glu Val
                820                 825                 830
Val Gln Gly Ala Tyr Arg Ala Ile Arg His Ile Pro Arg Arg Ile Arg
            835                 840                 845
Gln Gly Leu Glu Arg Ile Leu Leu
        850                 855

<210> SEQ ID NO 10
<211> LENGTH: 123
<212> TYPE: PRT
<213> ORGANISM: Human imunodeficiency virus type 1

<400> SEQUENCE: 10

Met Gly Gly Lys Trp Ser Lys Ser Ser Val Val Gly Trp Pro Ala Val
1               5                   10                  15
Arg Glu Arg Met Arg Arg Ala Glu Pro Ala Ala Asp Gly Val Gly Ala
                20                  25                  30
Ala Ser Arg Asp Leu Glu Lys His Gly Ala Ile Thr Ser Ser Asn Thr
            35                  40                  45
Ala Ala Asn Asn Ala Asp Cys Ala Trp Leu Glu Ala Gln Glu Glu Glu
        50                  55                  60
Glu Val Gly Phe Pro Val Thr Pro Gln Val Pro Leu Arg Pro Met Thr
65                  70                  75                  80
Tyr Lys Ala Ala Val Asp Leu Ser His Phe Leu Lys Glu Lys Gly Gly
                85                  90                  95
Leu Glu Gly Leu Ile His Ser Gln Arg Arg Gln Asp Ile Leu Asp Leu
                100                 105                 110
Trp Ile Tyr His Thr Gln Gly Tyr Phe Pro Asp
            115                 120

<210> SEQ ID NO 11
<211> LENGTH: 6
<212> TYPE: PRT
<213> ORGANISM: Human immunodeficiency virus type 1

<400> SEQUENCE: 11

Glu Leu Asp Lys Trp Ala
1               5
```

HIV-VACCINES

This application is a divisional of U.S. application Ser. No. 08/478,536 filed on Jun. 7, 1995 which issued as U.S. Pat. No. 5,911,989, which is a Continuation-in-Part Application of PCT International Application No. PCT/EP95/01481 filed on Apr. 19, 1995 under 35 U.S.C. § 371, the entire contents of each of the above identified applications are herein incorporated by reference.

BACKGROUND OF THE INVENTION

1. Technical field

The present invention is in the field of immunology, especially detection, prevention and treatment of HIV-1 infection and AIDS therapy. More particularly, it concerns monoclonal antibodies, drugs and vaccines made from these antibodies and methods based on the use of these antibodies, drugs and vaccines for analytical and/or clinical applications.

2. Description of Related Art

In the sera of human immunodeficiency virus type 1 (HIV-1) infected patients, anti-virus antibodies can be detected over a certain period after infection without any clinical manifestations of the acquired immunodeficiency syndrome (AIDS). At this state of active immune response, high numbers of antigen-specific B-cells are expected in the circulation. These B-cells are used as fusion partners for the generation of human monoclonal anti-HIV antibodies.

Monoclonal antibodies can be produced by known procedures, e.g., as described by R. Kennet et al. in "Monoclonal Antibodies and Functional Cell Lines; Progress and Applications". Plenum Press (New York), 1984.

Further materials and methods applied are based on known procedures, e.g., such as described in J. Virol. 67:6642–6647, 1993.

Monoclonal antibodies and in particular human monoclonal antibodies have been widely used in the last few years in order to improve the understanding of HIV-1 neutralization by antibodies released upon immunization with HIV-1 derived immunogens or upon infection in afflicted patients (J. Virol. 62:2107–2114, 1988; Immunology 76;515–534, 1992; J. Virol. 67:6642–6647, 1993; U.S. Pat. No. 5,087, 557). Many efforts have been made to overcome the detrimental capability of the HIV-1 virus to rapidly charge its morphology under immunological pressure and thereby to escape the capture by antibodies released from a patient's immune systems or developed and applied by researchers, As a result thereof, there is presently no reliable antibody-leased (nor any other) vaccine for active or passive immunization on the market. One significant step forward has been made when an antigens determinant on the smaller subunit gp41 of the HIV-1 envelope glycoprotein gp160 was found (EP 570 357 A2), which corresponds to the amino acid sequence "ELDKWA" (SEQ ID NO:11) located at amino acid position number 662 to 667 of gp41 of HIV-1 isloate BH10. The authors report therein an HIV-1 neutralizing human monoconal antibody specifically binding to said antigenic determinant. The antibody proved to be a powerful tool for biochemical analysis of the binding epitome and its variability, The discovery of the highly conserved state of said gp41-epitope gave rise to the hope of possibly finding a vaccine composition suitable for more reliable prevention of human individuals from HIV-1 infection and/or for more successful therapeutic treatment of infected patients.

The results reported in EP 570 357 A2 motivated the present inventors to intensify their research activities which finally led them to the novel and inventive findings herein disclosed.

However, in spite of promising results of the art relating to the use of HIV-1 neutralizing monoclonal antibodies, there is at least one major drawback to this sort of approach. It lies in the wide-spread use of laboratory strains of HIV-1 isolates, which have become adapted to lab-conditions and are more or less attenuated and hence only poorly—if at all—representative of the properties and behaviour of primary HIV-1 isolates. Consequently, promising vaccine compositions drawn against laboratory HIV-1 strains frequently proved non-efficacious when applied against primary HIV-1 isolates, e.g., of blood samples of infected persons (see J. Cohen, Science 262:980–981, 1993).

The second major drawback was and still is the ability of the HIV-1 virus to escape antibody capture by morphological variation, which very often renders the remarkable efforts of the researchers almost useless. Such escape mutants may be characterized by a change of only one or several of the amino acids within one of the targeted antigenic determinants and may occur, e.g., as a result of spontaneous or induced mutation.

SUMMARY OF THE INVENTION

The present invention therefore provides antibodies which have been found to overcome the disadvantages of the prior art and which can be used for the manufacture of vaccines for active and/or passive immunization of persons in need of such treatment. Such beneficial antibodies are, for instance, produced by any one of the cell lines CL1 through CL6 listed below. The invention also provides for human monoclonal antibodies that are functionally equivalent to the antibodies of CL1 through CL6. These functionally equivalent antibodies substantially share at least one major functional property with an antibody of CL1 to CL6 as herein described, comprising: binding specificity to gp160; bindinig dependence on glycosylation; reactivity in the presence of tunicamycin; inhibition of infections of human lymphocytes by primary HIV-1 isolates; reactivity towards antiidiotypes; competition for same binding site; reduction of the HIV-1 level in blood serum after intravenous administration to an infected patient; and/or specific binding to HIV-1 neutralizing antibodies.

It is also an object of the present invention to provide for the hybridoma and/or CHO cell lines producing any one of the antibodies disclosed and claimed herein.

The invention is further directed to mixtures of antibodies according to the present invention, as well as to methods of using individual antibodies or mixtures thereof for the prevention and/or therapeutical treatment of HIV-1 infections in vitro and in vivo, and/or for improved detection of HIV-1 infections.

The cell lines CL1 to CL4 produce monoclonal antibodies recognizing HIV-envelope glycoproteins, and in particular specific antigenic determinants of gp160. The antibodies of CL1 and CL4 recognize and bind to an amino acid sequence of gp41/gp160 corresponding to the epitope located at amino acid position number 662 to 667 ("ELDKWA") of gp41 of HIV-1 isloate BH10 (GenBank accession M15654; (SEQ ID NOS:1–10) numbering as described in the Swissprot database entry ENV$HIV10). The monoclonal antibodies of CL2 and CL3 bind to two different antigenic determinants, more particularly to fragments of gp120/gp160 corresponding to the epitope sequences located at amino acid positions 79 to 184 and 326 to 400 respectively, of processed gp120 of HIV-1 isolate BH10 (GenBank accession M15654; numbering as described in the Swissprot database entry ENV$HIV10).

While the idiotypic antibodies produced by CL1 to CL4 are directed to the capture and neutralization of HIV-1 viruses in vitro and in vivo, the antiidiotypic antibodies released from CL5 and CL6 take an opposite role, i.e., they mimic the viruses, more particularly they mimic the corresponding antigenic determinant(s) of the HIV-1 viruses. The anti-idiotypic antibodies of CL5 and CL6 are of a nature such that they bind to the idiotypic antibody of CL2 at essentially the same location(s) (antigenic determinants) on gp160 as does the virus itself.

BRIEF DESCRIPTION OF THE DRAWINGS

FIG. 2A shows the failure of a CL2 antibody to bind to the deglycosylated form (lane 3) of gp160 of HIV-1, while MAb CL1 (FIG. 2B) was used as a control because it successfully binds to the deglycosylated gp160;

DETAILED DESCRIPTION OF THE INVENTION

Figure 1:
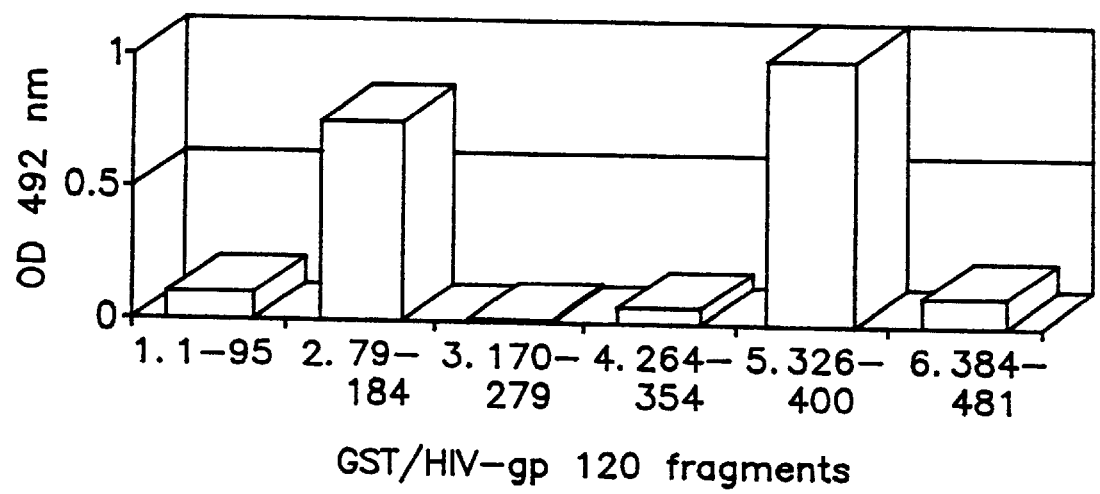
FIG. 1 shows the specific binding of a human monoclonal antibody released by hybridoma cell line CL2 with two distinct fragments of glycoprotein subunit gp120 of HIV-1; the numerals indicate the position numbers of the amino acids of the gp120 fragments as herein described.

The contents of each of the references cited herein are herein incorporated by reference in their entirety.

When conducting experiments to find novel anti-HIV-1 antibodies the inventors found human monoclonal antibodies which could be shown to efficiently neutralize HIV-1 in vitro including a variety of primary HIV-1 isolates, such as, e.g., primary HIV-1 isolates 92 RW009, 92RW021, 92UG037, 92TH014, 92BR030, N70-2, DJ259 (all obtained from WHO network for HIV-1 isolation and characterization), or WYG, WRF, WRB, WSC, WHM (isolated from Austrian patients).

Surprisingly, it turned out that these antibodies recognize and bind to two different antigenic determinants of the glycoprotein gp160 of HIV-1.

Moreover, it appears that the binding target of these antibodies is extraordinarily unique. In a comparative test involving a mixture of 41 different HIV-1 binding antibodies supplied by laboratories from different companies and research institutes, it was shown that no one of the other antibodies present in the mixture competed with an antibody of the above-identified group, for instance with the human monoclonal antibody from cell line CL2, for binding to the targeted antigenic fragments of gp120/gp160 corresponding to amino acid sequences 79 to 184 and 326 to 400 of processed gp120 of HIV-1 isolate BH10.

Also, investigations of blood serum and blood plasma of HIV-1 infected patients revealed that antibodies of the CL2 type were not present in the samples tested so far. This finding again emphasizes the uniqueness of these HIV-1 neutralizing human monoclonal antibodies and simultaneously indicates that there might exist an extraordinary potential to combat HIV-1 infection, by using these antibodies in a suitable form for the prophylactic and/or therapeutic treatment of human individuals.

Another object of the present invention relates to antibodies of the CL2 type which have been found to bind to the above-mentioned antigenic determinants of gp120/gp160 only if the determinants are present in a glycosylated form; they do not bind to these antigenic glycopeptide fragments when the fragments are deglycosylated, e.g., by the action of Peptide-N-Glycosidase F (EC 3.2.2.18; hereinafter referred to as "PN Gase F").

Still another object of the present invention encompasses human monoclonal antibodies of the CL2 type which are further characterized in that they also specifically bind to a fragment of gp120 produced in the SF9 insect cell/Baculovirus expression system in the absence of tunicamycin, while they do not bind to gp120 fragments expressed in the presence of tunicamycin. Tunicamycin is known for its inhibitory activity toward the glycosylating action of glycosyl transferase in glycoprotein biosynthesis.

Among the antibodies of the CL2 type as disclosed herein, there are also types which inhibit the infection of human lymphocytes by primary HIV-1 isolates such as the ones listed herein, as could successfully be demonstrated by the inventors in in vitro experiments.

The present invention also relates to antibodies of the CL2 type which possess one or more of the above-mentioned properties and which can further be characterized by their special interaction with the anti-idiotypic monoclonal antibodies of hybridoma cell lines CL5 and CL6. While they can be bound by one and/or the other of the two anti-idiotypic antibodies CL5 and CL6, at least part of them is bound by anti-idiotypic huMAb produced by CL6 in a way that results in a specific blockade of the capability of the antibody to inhibit the infection of human lymphocytes by primary HIV-1 isolates.

A further object of the present invention comprises antibodies of the CL2 type which show at least one of the above-mentioned features or properties and which—in addition—have been proved to compete for binding to the antigenic determinants of gp120/160 with the antibody produced by hybridoma call line CL2. The antibodies of this category are therefore—at least functionally—very closely related with the antibody released by CL2, and can be regarded as functional equivalents to it.

Another object of the present invention is directed to the most beneficial human monoclonal antibody produced by hybridoma cell line CL2. This antibody can be used, e.g. for passive immunization of HIV-1 infected individuals, but may even be more useful as a biochemical tool for developing vaccines applicable in the prevention and/or therapy of HIV-1 infections in vivo.

An attractive object of the present invention comprises the use of recombinant CHO cells for the production of the antibodies of the CL2 type. After successful identification of the antigenic determinants recognized and bound by these antibodies, the inventors also succeeded in transforming the respective genetic information into CHO cells, resulting in a stable cell line CL3, which synthesizes the CL2 type antibodies in a more efficient manner than the hybridoma cell line CL2 itself.

In another embodiment, anti-idiotypic antibodies are disclosed which can specifically bind to idiotypic antibodies of the CL2 type and/or which can interact with at least some of them in a fashion that eliminates their anti-HIV protective capability, i.e., bars them from inhibiting the infection of human lymphocytes by primary HIV-1 isolates. Such anti-idiotypic antibodies are therefore expected to be conformationally related to the HIV-1 viruses in that they probably contain similar or even identical antigenic fragments of a viral glycoprotein, e.g., of gp160.

The antibodies of the next embodiment seem to be very interesting because they are of an anti-idiotypic type and combine the features of the anti-idiotypic antibodies of the previous embodiment with their ability to induce—upon administration to a mammal, e.g., a human or animal individual—the production and release of anti-HIV-1 antibodies. Optionally, the induced antibodies are of a nature such that they compete for binding to the above specified antigenic determinants of gp120/160 with at least one antibody of the CL2 type as hereinbefore described in any one of the respective embodiments. A special representative of this group of anti-idiotypic antibodies is the one produced by hybridoma cell line CL6.

While the anti-idiotypic antibodies of the preceding embodiment may be used for active immunization of test animals or HIV-1 endangered and preferably not yet infected persons, the antibodies induced upon such active immunization may serve as components of a vaccine for passive immunization or as subjects of investigation to design and/or synthetically or genetically prepare such antibodies. Optionally, these (idiotypic) antibodies are functional equivalents to the CL2 type antibodies, i.e., they compete with the CL2 type antibodies for binding to the above specified antigenic determinants of gp120/gp160.

In a further—most exciting—embodiment of the invention, the human monoclonal antibodies exhibit strong HIV-1 neutralizing activity and bind to the smaller subunit of gp160, hereinafter referred to as gp41/gp160. Preclinical studies have proved that they are able to significantly reduce—upon intravenous administration to a human HIV-1 infected individual—the level of circulating HIV-1 in the blood serum and/or blood plasma of said individual (see Example 8 and FIG. 6).

Moreover, at least part of these antibodies may be further characterized in that they also compete with an idiotypic antibody produced by hybridoma cell line CL1 for binding to the gp41/gp160 antigenic determinant. Finally, the antibody produced by said cell line CL1 itself can be regarded as an important member of this group of HIV-1 level reducing antibodies.

Similarly to the situation with the CHO cell line CL3 producing CL2 type antibodies, the inventors also succeeded in cloning a recombinant CHO cell line CL4 producing antibodies which compete with the antibody of CL1 for binding to the gp41/gp160 antigenic determinant and hence may be regarded as more or less close equivalents to the CL1 antibody. Such recombinant CHO cell lines are easier to grow and more efficiently employed in the manufacture of the respective antibodies.

Various in vitro experiments have proved that the CL2 type antibodies as well as tile CL1 type antibodies are able to neutralize a variety of different laboratory and primary HIV-1 isolates including a number of escape mutants, which usually develop upon individual application of any one of these antibodies. It could further be shown that both antibody types are cross-reactive, i.e., they interact synergistically in that each of them is able to capture the escaped HIV-1 mutants of the other antibody. Combined in a mixture, they are therefore a powerful tool to combat HIV-1 infections and AIDS. It is one of the objects of the present invention to provide for a mixture of at least one antibody of the CL1 type and at least one antibody of the CL2 type.

The present invention also relates to a cell line producing any one of the antibodies described above, and in particular, to the cell lines CL1 through CL6 identified by their accession numbers as described below. Viable samples of the hybridoma cell lines CL1 to CL6 producing the monoclonal antibodies herein described were deposited at the European Collection of Animal Cell Cultures (ECACC) at the Public Health Laboratory Service (PHLS), Centre for Applied Microbiology and Research, Porton Down, Salisbury SP4 OJG, United Kingdom. They are identified by their accession numbers:

CL1—Accession No. 90091704 (deposited on Sep. 17, 1990);

CL2—Accession No. 93091517 (deposited on Sep. 15, 1993);

CL3—Accession No. 95032235 (deposited on Mar. 22, 1995);

CL4—Accession No. 95032236 (deposited on Mar. 22, 1995);

CL5—Accession No. 95032240 (deposited on Mar. 22, 1995); and

CL6—Accession No. 95032241 (deposited on Mar. 22, 1995).

The corresponding monoclonal antibodies produced by these cell lines are hereinafter termed MAb CL1, MAb CL2 through MAb CL6, when used in the abbreviated form.

In a further embodiment of the present invention, peptide fragments are provided which contain at least one of the antigenic determinants of gp41/gp160 and gp120/gp160 as herein described. It is desired that these peptide fragments are of a nature such that they are able to induce an immune response against HIV-1 infection, optionally the production and/or release of HIV-1 neutralizing antibodies after administration to mammals, e.g., to an animal or a human individual.

In another embodiment, these peptide fragments may be linked to a suitable carrier in order to improve the efficacy of antigen presentation to the immune system. Such carriers may be, for instance, organic polymers including proteins, but any other appropriate and physiologically acceptable carrier may also be used, including tetanus toxoid, cholera toxin, keyhole limpet hemocyan, glutathions S-transferase and all viruses that can be modified by recombinant DNA technology such as, e.g. Rhino-, Polio-, Vaccinia-, or Influenzavirus, etc. It may be advantageous in many cases to have the peptide fragments linked to a modifies, i.e., attenuated and/or recombinant virus such as modified influenza virus or modified hepatitis B virus or to parts f a virus, e.g., to a viral glycoprotein such as, e.g., hemagglutinin of influenza virus or surface antigen of hepatitis B virus, in order to increase the immunological response against HIV-1 viruses and/or infected cells.

It is also an important object of the present invention to provide for the manufacture of a reliable vaccine to protect people from HIV-1 infection and/or to treat patients with already manifest HIV-1 infections in the course of a therapy. Vaccines based on at least one of the idiotypic antibodies of the CL2 and CL1 groups can be employed for active immunization in the prophylaxis and therapy of higher animals including man. Convincing evidence are provided below for the reduction of the HIV-1 level in the plasma and serum of a seropositive patient in the course of a therapeutic treatment in a preclinical study (cf. Example 8 and FIG. 6). Also, the preventive potency of the idiotypic antibodies of cell line CL1 was demonstrated in an impressive SCID-mouse trial as well as in a chimpanzee experiment. Neither the antibody-treated mice nor the chimpanzees developed HIV-1 infection upon challenge with live HIV-1 virus, while the animals in the untreated control groups became infected.

The use of at least one anti-idiotypic antibody as hereinbefore described for the manufacture of a vaccine for active immunization can help to successfully combat HIV-1 infection. The anti-idiotypic antibodies—as well as the drugs and vaccines derived therefrom—may primarily be used for the preventive treatment of HIV-1 endangered people and are optimally applied prior to coming into contact with HIV-1 virus. Due to their unique paratope characteristics they may also be administered to already infected patients in order to stimulate the immune system to release the corresponding—and possibly even more powerful—HIV-1 neutralizing antibodies. They may be either directly administered to a person or in combination with at least one suitable carrier and/or additive as usual in the art, and/or along with additional drugs such as, for instance, nucleoside analogues (e.g. AZT, ddl), cytokines (e.g. interleukins), HIV-protease inhibitors, antibiotics, etc. The anti-idiotypic antibodies may, however, also serve as “model templates” for the design and construction of, e.g., fusion proteins carrying their respective antigenic determinant(s) (paratopes).

It might be preferable in many cases to combine an individual antibody or a mixture of at least two different antibodies with an immunoserum and/or an antibiotic, in order to further improve the benefit of an antibody vaccine manufactured accordingly.

In other cases it might be advantageous to use at least one of the herein specified antigenic peptide fragments of gp41/gp160 and gp120/gp160 to substitute the anti-idiotypic antibodies in the corresponding vaccines and drugs. Therefore the present invention also relates to said peptide fragments and to the use thereof for the manufacture of drugs and/or vaccines applicable in the prophylactic and/or therapeutic treatment of HIV-1 endangered or HIV-1 infected people. The fragments are preferably applied as fusion proteins, wherein they are linked to a suitable carrier which might be a recombinant or attenuated virus or a part of a virus such as, e.g., the hemagglutinin of influenza virus or the surface antigen of hepatitis B virus, or another suitable carrier including other viral surface proteins, e.g., surface proteins of Rhinovirus, Poliovirus, Sindbis virus, Coxsackievirus, etc., for efficient presentation of the antigenic site(s) to the immune system. In some cases, the antigenic fragments might, however, also be purely, i.e., without attachment to a carrier, applied in an analytical or therapeutical program. It is of considerable benefit that the fragments can be used for the prevention and/or treatment of HIV-1 infections in human individuals such as persons belonging to one of the high-risk groups of HIV-1 endangered people including medical and scientific staff dealing with HIV-1 viruses and/or infected individuals.

The idiotypic antibodies referred to herein may further be used for the detection and/or determination of HIV-1 infected cells and/or HIV-1 viruses, either as individual antibodies or as an antibody cocktail. Similarly, one or more of the anti-idiotypic antibodies and/or the above-specified peptide fragments can successfully be applied to detect and/or determine anti-HIV-1 antibodies binding to the viruses or to HIV-1 infected cells. Both the idiotypic and anti-idiotypic antibodies of the present invention may therefore be prepared and arranged for an analytical testing procedure and/or for a commercially utilizable test kit.

Finally, it is also an object of the present invention to provide a method of treating HIV-1 infected persons in need of such treatment, and to provide for a method of preventing people from becoming HIV-1 infected. Patients with manifest HIV-1 infections may be therapeutically treated with a vaccine comprising at least one of the idiotypic antibodies of the CL2 and the CL1 type, preferably a mixture thereof. However, in some cases it might be preferable to administer at least one of the anti-idiotypic antibodies and/or antigenic peptide fragments in order to induce additional—possibly even more powerful—antibodies to neutralize the viruses and to reduce the HIV-1 levels in the blood of infected patients.

The vaccine based on antibodies and/or antigenic peptide fragments may further comprise suitable, i.e., physiologically acceptable, carriers—preferably for the preparation of injection solutions—and further additives as usually applied in the art (stabilizers, preservatives, etc.), as well as additional drugs. The patients may be adminstered a dose of approximately 1 to 10 μg/kg body weight, preferably by intravenous injection once a day. For less threatening cases or long-lasting therapies the dose may be lowered to 0.5 to 5 μg/kg body weight per day. The treatment may be repeated in periodic intervals, e.g., two to three times per day, or in daily or weekly intervals, depending on the status of the infection.

Vaccines according to the present invention may comprise any one of the idiotypic or anti-idiotypic antibodies or any one of the peptide fragments disclosed herein, either alone or in combination with suitable carriers and/or linked to carrier molecules. In some cases, e.g., where HIV-1 infection is acute and/or has already considerably progressed, it might be preferable to apply a mixture of idiotypic antibodies, while in other cases it might be more beneficial to apply a mixture of anti-idiotypic antibodies and/or—preferably carrier-linked—gp160 peptide fragments. It is recommended to apply a dose of 0.5 to 10 μg/kg body weight of antibody or carrier-linked gp160 peptide fragments, administered once to three times a day and possibly repeated in periodic intervals, e.g., weekly, monthly or yearly intervals, depending on the status of HIV-1 infection or the estimated threat of an individual of getting HIV infected.

In order that the invention described herein may be more fully understood, the following examples are set forth. It should be understood that these examples are for illustrative purposes only and a riot to be construed as limiting this invention in any respect.

EXAMPLE 1 (FIG. 1)

Reactivity of GST/HIV-gp120 Fusion Proteins with Antibodies from Cell Line CL2

The binding characteristics of the human monoclonal antibody produced by CL2 (referred to hereinafter as MAb CL2) to the HIV-1 envelope glycoprotein gp120:

Overlapping gp120 fragments were fused to Glutathione S-tranferase (GST) and expressed using the insect cell/baculovirus system. Cell lysates of SF9 cells infected with recombinant baculovirus clones expressing different GST-gp120 fragments were first tested for their production level of GST. Lysates of GST-gp120 fusion proteins were then analysed in order to determine the binding affinity of MAb CL2. OD values of MAb CL2 given in the figure correspond to different rgp120 fragments. Microtiter plates were precoated with 2 μg/ml glutathione, cell lysates were added and incubated for 1 hour followed by an incubation step of 1 hour with 1 μg/ml MAb CL2 and detection with horseradish peroxidase conjugated anti-human IgG. The optical densities of the cell lysates corresponding to an equal amount of the GST fusion protein are shown.

In FIG. 1, GST-fusion-protein containing fragment 1 corresponds to amino acids 1–95 of processed gp120 of the BH10 isolate of HIV-1, fragment 2 corresponds to amino acids 79–184 of gp120, fragment 3 to amino acids 170–279, fragment 4 to amino acids 264–354, fragment 5 to amino acids 326–400 and fragment 6 to amino acids 384–481. FIG. 1 demonstrates that MAb CL2 binds to two different fragments of gp120, namely to fragment 2 (amino acids 79–184) and to fragment 5 (amino acids 326–400).

EXAMPLE 2 (FIG. 2)

Antibody Binding to Deglycosylated gp160$_{HIV\ MN}$

For N-deglycosylation protein samples (500 ng recombinant gp160 of HIV-1 isolate MN) were boiled 10 min. in denaturation buffer (0.5% SDS, 1% β-Mercaptoethanol). Then 1/10 volume each of 10× enzyme reaction buffer and 10% NP-40 (polyglycol ether surfactant; Tergitol®) were added. This reaction mixture was incubated with 2000 U of PNGaseF (Boehringer Mannheim) for 12 hours at 37° C. Polyacrylamide gel electrophoresis was performed on gels in 10–20% Tris/Glycin . After protein blottifig, identical membranes were incubated with 5 μg/ml MAb CL2 (panel A), and 5 μg/ml MAb CL1 (panel B) as control.

Figure 2:
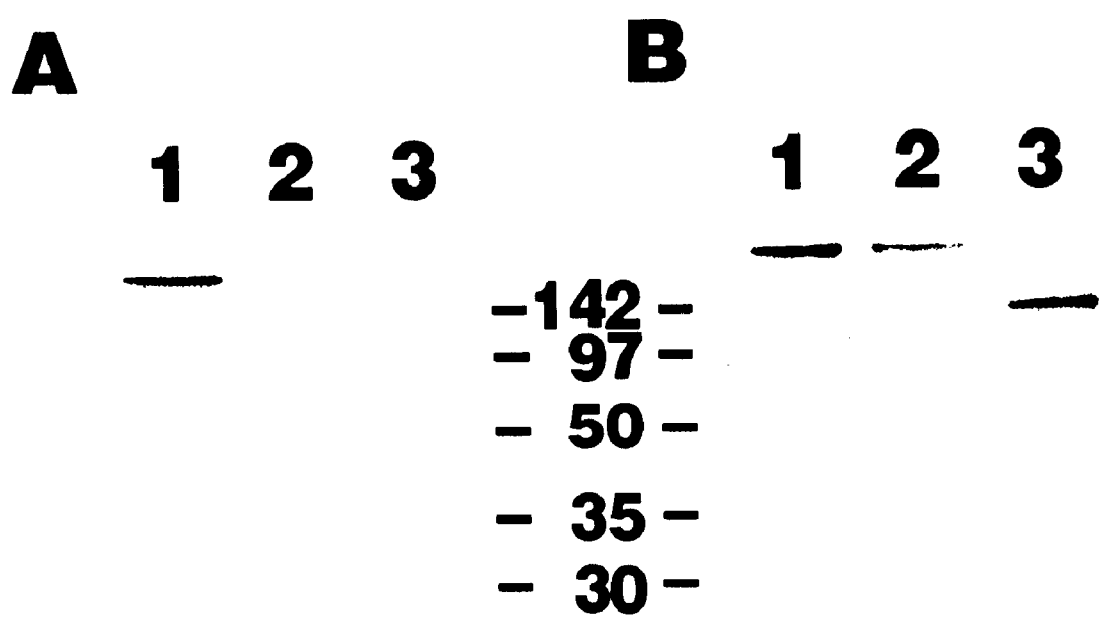

In FIG. 2 lanes 1 to 3 contain the following:

lanes 1: untreated gp160$_{HIV\ MN}$;

lanes 2: gp160$_{HIV\ MN}$ conditioned for PNGaseF treatment without enzyme;

lanes 3: gp160$_{HIV\ MN}$ PNGaseF treated;

molecular weight markers are indicated in kDa,

It can be seen in FIG. 2 that MAb CL2 does not bind to gp160 after the deglycosylating action of PNGaseF (panel A, lane 3), while MAb CL1 binds to the PNGaseF treated gp160 (panel B, lane 3).

EXAMPLE 3 (FIG.3)

Reactivity of Recombinant GST/HIVgp120 Fusion Protein with MAb CL2 and anti-GST Antiserum in the Presence and Absence of Tunicamycin (TM)

SF9 insect-cells were infected with either wildtype baculovirus or GST-gp120 expressing recombinant baculovirus. 5 hours after infection, tunicamycin was added to a final concentration of 5 μg/ml. Cells were harvested after 48 hours and lysed. Anti-GST reactivity and MAb CL2 reactivity were tested by ELISA. Baculovirus infected cell-lysates (obtained from 1×10$^7$ cells/ml) were transferred to microtiter plates, which were precoated with 2 μg/ml glutathione and incubated for 1.5 hours. GST-fusion protein or gp120 was detected by GST-antiserum (diluted 1:2000) or MAb 2G12 (1.5 μg/ml), respectively, and horseradish peroxidase conjugated anti-mouse/anti-human IgG. The absorbance was determined at 492 nm.

Figure 3:
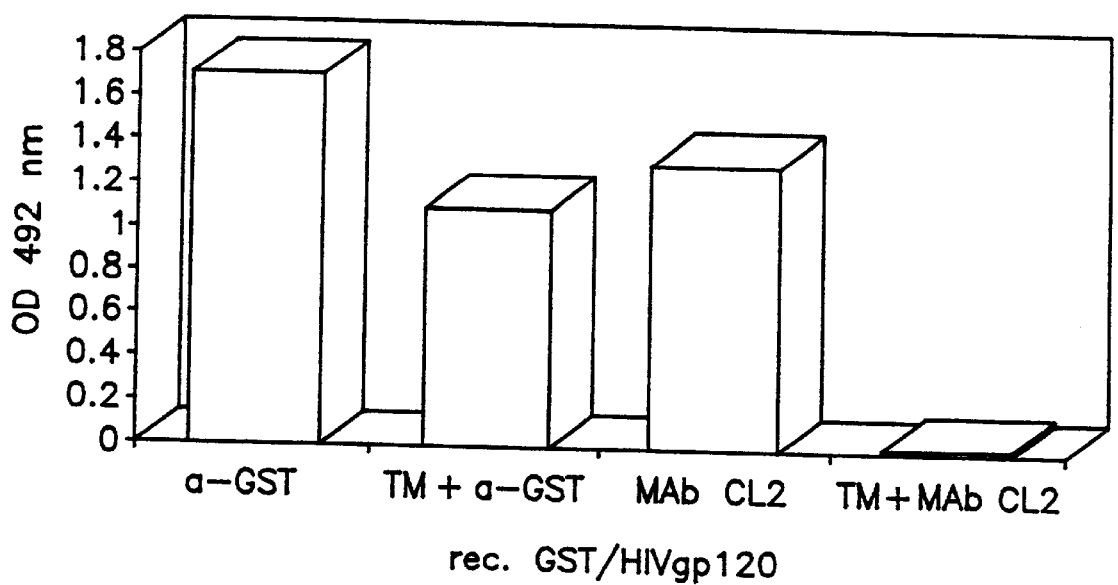
FIG. 3 shows the reactivity of anti-GST antiserum and a CL2 antibody with a recombinant gp120 in the presence and absence of tunicamycin, while a-GST binds to rec.GST/HIVgp120 in the presence of tunicamycin (at a reduced level) the CL2 antibody does not (bar 4)

As can be seen in FIG. 3 MAb CL2 does not bind to the gp120 fusion protein in the precence of tunicamycin, whereas anti-GST does, although at a decreased level.

EXAMPLE 4

Neutralization Capacity of MAb CL2 for Primary HIV-1 Isolates

A PBMC (=peripheral blood mononuclear cells) based neutralization assay was performed as described by Purtscher et al. (M. Purtscher et.al.,1994. Aids Research and Human Retroviruses. 10/12: 1651–1658, Mary Ann Liebert, Inc., Publ., 1994) by pre-incubating virus with serial antibody dilutions for 1 h at 37° C. and subsequent infection of fresh PHA (=phytohemagglutinin) stimulated PBMC prepared from HIV-negative donor buffy-coat cells. Neutralization capacity was estimated after 7 to 12 days by comparing the amounts of p24 antigen produced by the cells in the presence or in the absence of antibody.

TABLE 1

Summary of neutralization capacity of MAb CL2 in neutralization assays using PBMC

| primary isolate | subtype clade | neutralizing capacity |
|---|---|---|
| 92RW009 | A | +++ |
| 92RW021 | A | +++ |
| 92UG037 | A | +++ |
| 92TH014 | B | +++ |
| 92BR030 | B | +++ |
| N70-2 | B | + |
| DJ259 | C | + |
| WYG | unknown | +++ |
| WRF | unknown | +++ |
| WRB | unknown | +++ |
| WSC | unknown | + |
| WHM | unknown | + |

Key:
+++ 90% neutralization at a conc. of <1 μg/ml
++ 90% neutralization at a conc. between 1 to 50 μg/ml
+ 50% neutralization at a conc. below 50 μg/ml

EXAMPLE 5 (FIG. 4)

Syncytia Inhibition Assay/Anti-idiotype Blocking

An anti-idiotype (Ab2) blocking assay was performed to determine whether the anti-idiotypic antibodies Ab2 block the neutralization capacity of MAb CL2 by binding to the neutralizing paratope of MAb CL2. The syncytia inhibition concentrations (EC$_{50}$) of MAbs CL1 and CL2 in the absence of anti-idiotypic antibodies were 2.0 and 8.8 μg/ml, respectively (the HIV-1 isolate RF was used). The addition of anti-idiotypic antibodies to MAb CL2 revealed that the antibodies M1A3 and M4C12 did not alter the neutralizing capacity, but when M1G1 (=anti-idiotypic antibody produced by CL6) was incubated with MAb CL2 a significant impairment could be observed (Table 2). The syncytia inhibiting capacity of MAb CL1, which is directed against gp41, should not be affected by the anti-idiotypic antibodies tested. No syncytia inhibition was observed with anti-idiotypic antibodies alone at a concentration of 100 μg/ml as well as with MAb 3D6, which was used as a non-neutralizing control.

TABLE 2

EC$_{50}$ of MAb CL2 and MAb CL1 in the presence of M1G1, M1A3 or M4C12

| | | anti-idiotype added (μg/ml) | | |
|---|---|---|---|---|
| MAb | alone | + M1G1 (= MAb CL6) 100 | + M1A3 (= MAb CL5) 100 | + M4C12 100 |
| MAb CL2 | 2.02 | 5.26 | 2.63 | 0.66 |
| MAb CL1 | 8.83 | 7.43 | 8.83 | 6.25 |

Anti-idiotypic antibodies were diluted to 200 μg/ml and MAbs CL2 and CL1 (as control antibody) were diluted to 10 μg/ml in RPMI 1640 medium 50 μl of serial two-fold dilutions of MAbs CL2 and CL1 were prepared starting at 100 μg/ml in four replicates. 50 μl of anti-idiotypic antibody (200 μg/ml) were added to each well and pre-incubated for 1 h at 37° C. in the incubator. As virus inoculum the HIV-1 isolate RF was diluted to approximately 10$^2$–10$^3$ TCID$_{50}$/ml and 50 μl of the virus suspension were added to each well. After an incubation of 1h at 37° C., 50 μl of AA-2 cell suspension ($10^6$ cells per ml; see CHAFFEE et al, 1988, J.Exp.Med. 168:605–621) were added to each well. The cells were then cultivated during 5 days at 37° C. and 5% $CO_2$, followed by microscopical evaluation of syncytia formation. Occurrence of at least one syncytium per well was recorded as an indication of HIV-1 infection. The 50% effective concentration ($EC_{50}$) was calculated by the method of Reed and Muench (Reed, L. J. and Muench, H. 1938. A simple method of estimating fifty percent endpoints. Am.J.Hyg.27:493–497).

Figure 4A:
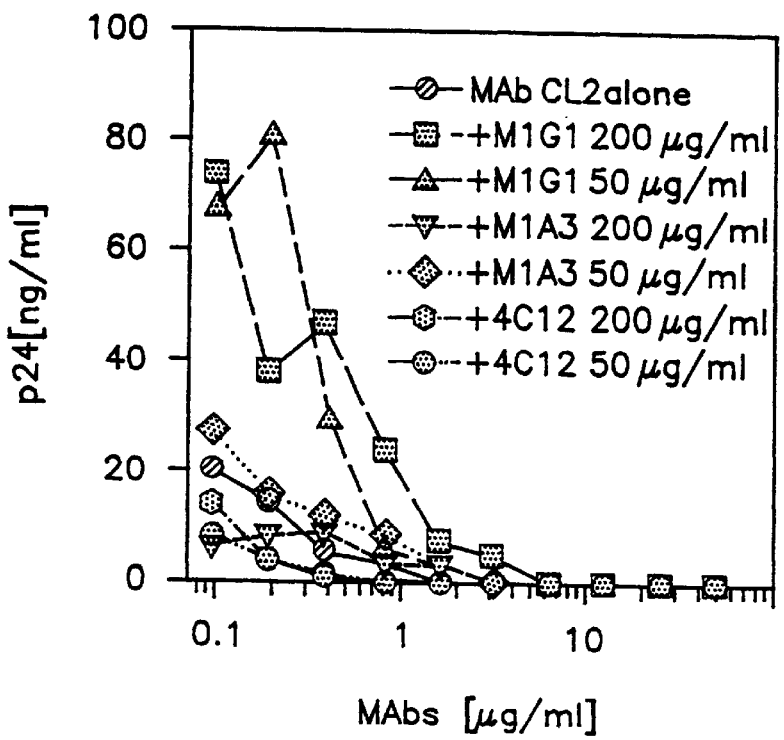
FIG. 4A shows the blocking effect of antibodies M1G1 through 4C12 toward HIV-1 neutralizing monoclonal antibodies of the CL2 (plot A) and CL1 (FIG. 4B) cell line in a p24 antigen ELISA; the anti-idiotypic character of M1G1 towards MAb CL2 is demonstrated.
Figure 4B:
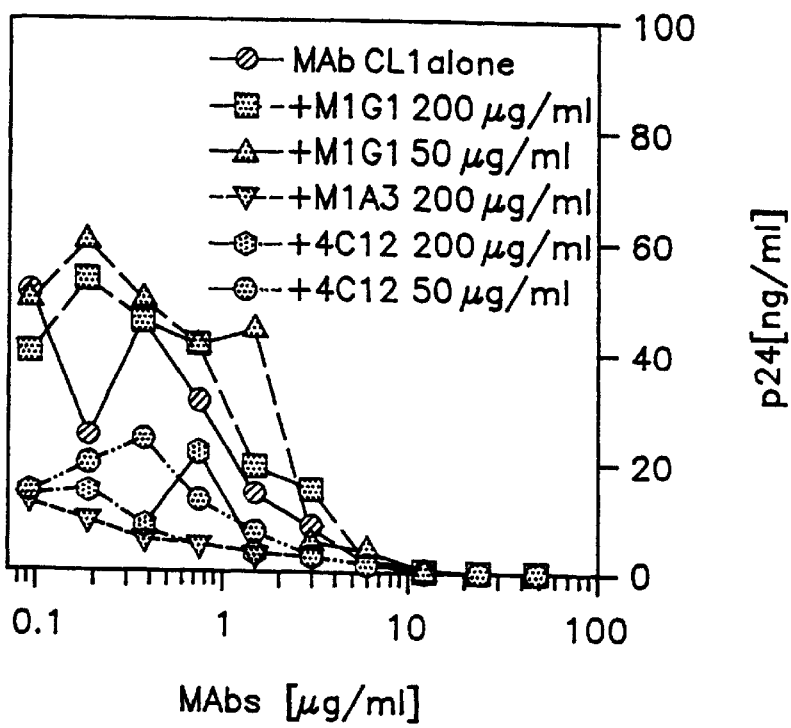

All wells of one dilution step were then pooled and p24 was determined quantitatively in a p24 antigen ELISA. The measured p24 values were plotted against the MAb concentration. The results thereof can be seen in FIG. 4 which displays the production of antigen p24 in cultures containing MAb CL2 (graph A) and MAb CL1 (graph B) with different amounts of anti-idiotypic antibodies. Contrary to M1A3 (=MAb CL5) and 4C12, M1G1 (=MAb CL6) inhibits the neutralization activity of MAb CL2 suggesting that M1G1 at least partly mimics the paratope (of HIV-1 gp120) corresponding to the epitope of MAb CL2. The control MAb CL1 is not inhibited by any of these antibodies. These results indicate that monoclonal antibody M1G1 is an antiidiotypic antibody to MAb CL2.

EXAMPLE 6 (FIG.5)

Figure 5A:
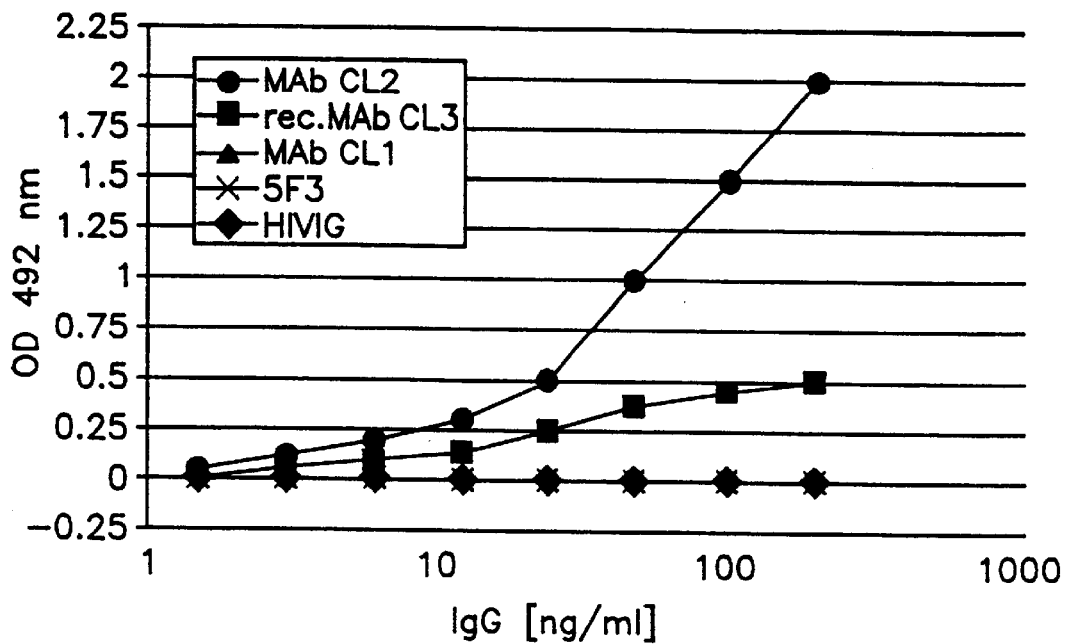
FIG. 5A shows the uniqueness of antibodies of the CL2 and the CL3 (=recomb. CL2) cell lines among a multitude of different anti-HIV antibodies; only the antibodies of CL2 and CL3 are recognized and bound by the antiidiotypic antibodies M1G1 (plot A) and M1A3 FIG. 5B.
Figure 5B:
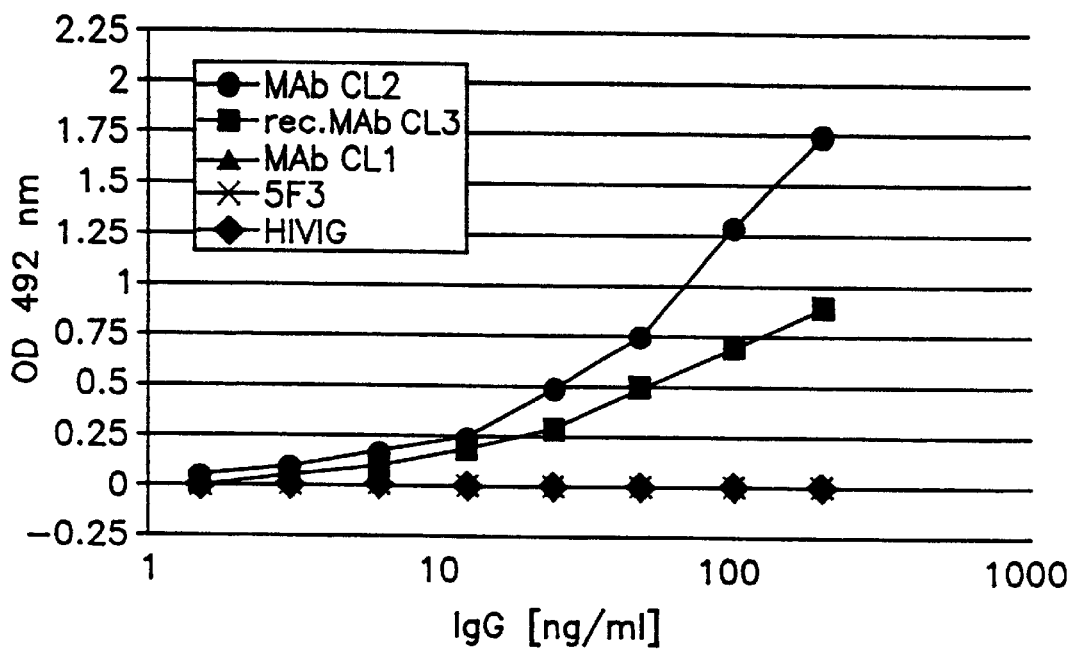

Reactivity of the Anti-idiotypic Antibodies with Different Anti-gp160 Antibodies A panel of human anti-gp160 antibodies and pooled serum of HIV-1 positive individuals (HIVIG) were incubated on gp160-coated microtiter plates in the presence of M1G1 (=MAb CL6) and M1A3 (=MAb CL5), to prove the reactivity of the anti-idiotypes. FIG. 5, graphs A and B, show the MAb CL2 specific binding of M1G1 (graph A) and M1A3 (graph B), respectively. Both anti-idiotypic antibodies were only reactive with MAb CL2 and its recombinant double (MAb CL3) but not with other tested human antibodies (MAb CL1 and 5F3 and HIVIG are representative examples of human anti-HIV-1 antibodies).

FIG. 5, graphs A and B: 96-microtiter plates were coated with 2 $\mu$g/ml gp160 (Immuno AG, Vienna). Starting dilution of the human monoclonal antibody samples began at a concentration of about 200 ng/ml and HIVIG was prediluted 1:100. Eight dilutions of the human antibodies were preformed in $2^n$ steps. M1G1 and M1A3 were used at a concentration of 1 $\mu$g/ml. The human and murine antibody dilutions were transferred to the test plate and simultaneously incubated for 1 h. Then peroxidase-conjugated goat anti-mouse IgG was applied to the plate. After 1 h of incubation staining solution was added to each well; the absorbances were read at 492 nm against 620 nm.

EXAMPLE 7

Immune Selection Experiments with HIV-1 Molecular Clone cl82.

Immune selection experiments with HIV-1 molecular clone cl82 in the presence of either MAb CL1 or MAb CL2 resulted in the generation of escape mutants at antibody concentrations lower than 6.3 $\mu$g/ml and 25 $\mu$g/ml, respectively, When both MAbs were present at the same time in the reaction mixtures virus variants evolved were only resistant to either MAb CL1 or MAb CL2. These results (Table 3) suggest that the virus cannot accumulate sufficient mutations to render itself resistant to both antibodies. Therefore, the emergence of HIV-1 escape mutants during treatment of HIV-1 infected individuals could be overcome by using a mixture of MAb CL1 and MAb CL2.

TABLE 3

| MAb | Selection conditions | | |
|---|---|---|---|
| | $\mu$g/ml | virus emerged | $EC_{50} > 50$ $\mu$g/ml |
| MAbCL1 | 25 | no | |
| | 6.3 | no | |
| | 1.6 | yes | + |
| | 0.8 | yes | + |
| MAb CL2 | 25 | no | |
| | 6.3 | yes | + |
| | 1.6 | yes | + |
| | 0.8 | ND | |
| MAb CL1 + CL2 | 25 | no | |
| (Mixture: 50/50) | 6.3 | no | |
| | 1.6 | no | |
| | 0.8 | 1) | – |
| | 0.4 | 2) | – |

ND, not done
1) neutralization resistant to MAb CL2; Mixture and MAb CL1 still neutralizing;
2) neutralization resistant to MAb CL1; Mixture and MAb CL2 still neutralizing.

EXAMPLE 8 (FIG. 6)

Course of p24 Production in Cultures with Serum Samples from an HIV-1 Infected Individual Before and after Treatment with 3 Doses of MAb CL1.

Serum was incubated with PHA-stimulated PBMC from healthy, HIV-negative blood donors. Twice a week, culture supernatant was changed 1:2 by removing half of the supernatant and substituting therefor an equal volume of fresh media. Once per week fresh PHA-stimulated PBMC were added to the culture, The culture was monitored for 5 weeks.

Figure 6:
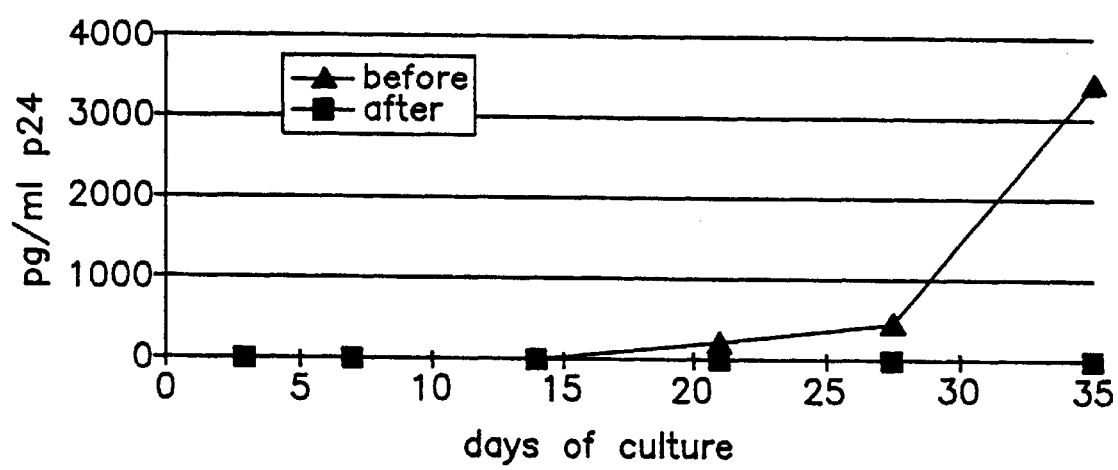
FIG. 6 shows HIV-1 neutralizing efficacy of antibodies of cell line CL1 after in vivo application to a human patient; triangles show the HIIV-induced formation of syncytia in the serum taken from an infected patient before administration of CL1 antibodies, while squares demonstrate complete failure of syncytia formation after administration of CL1 antibodies.

FIG. 6 shows the increase in syncytia formation of cultured serum samples taken from the patient before the administration of MAb CL1 (triangles) and the impressive neutralization of the pationt's HIV-1 infection upon administration of MAb CL1, as displayed by the horizontal line at the zero level of p24 production.

EXAMPLE 9

In Vivo Prevention of HIV-1 Infection in a Chimpanzee 4 chimpanzees have been selected for testing the in vivo neutralization in a collaboration with the Merck-research center in West Point, Pa. 19486, USA.

Prior to the in vivo test, CD4 positive primary T cells (PBMC's) were isolated from each chimpanzee to test the permissiveness of in vitro infection with the primary HIV-1 isolate, lade B. For all in vitro tests, conventional procedures as described in M. Purtscher et.al., Aids Research and Human Retroviruses, Vol. 10, Nr. 12, 1994, Mary Ann Liebert, Inc., Publ., have been used. The CD4 PBMC of all four chimpanzees were permissive to viral propagation in vitro. This was to prove that an in vivo infection should be successful.

Two of the chimpanzees were infused with the monoclonal antibody CL1 (PHLS Deposit No. 90091704). For the intravenous infusion of the antibodies 300 ml of solution containing approx. 1 mg/per mililiter stabilized in 1% human serum albumin, at pH 7 were applied per animal. Two other animals were only treated with human serum albumin.

All four chimpanzees were challenged one day after treatment with the primary HIV-1 isolate by intraveneous injection of 3 chimpanzee infective doses of the virus. All four animals were routinely tested for HIV-1 infection for a period of four months.

Result: The two chimpanzees treated with antibody CL1 showed no signs of HIV-1 infection; they have been protected from infection. Both control animals, i.e., those treated only with human serum albumin, became HIV-1 positive.

EXAMPLE 10
In Vivo Prevention of HIV-1 Infection in a SCID-mouse Trial

Another experiment to demonstrate the in-vivo neutralization ability of MAb CL1 has been carried out in collaboration with Transgene, Strasbourg, France, The genes encoding the heavy and light chains of MAb CL1 have been supplied to Transgene to genetically manipulate mouse fibroblasts (3T3) using standard genetic engineering techniques. The transformed mouse fibroblasts producing MAb CL1 were propagated in vitro on GOREDEX® fibres to form cell pellets. The cell pellets were then applied under the skin of SCID mice to form organelles within these mice so as to release the MAb CL1 into the blood stream.

The SCID-mice were reconstituted using conventional procedures with the human white blood cell system in order to give an animal model suitable for infection by HIV-1.

Those SCID-mice having a level of MAb CL1 higher than 2 micrograms of antibody per ml serum were protected against a challenge with HIV-1 IIIB, whereas those having a lower level of antibody per ml in the serum showed a significant delay of infection. SCID-mice treated otherwise in an analogous way and having no MAb CL1 in their serum were all infected.

EXAMPLE 11
Detection of HIV-infection by Means of HIV-1 Peptide Fragments and/or Antiidiotypic Antibodies Peptide fragments according to the present invention containing at least one of the antigenic determinants of gp41/gp160 and gp120/gp160 as herein described and/or antiidiotypic antibodies recognizing and binding to the epitope of MAb CL1 or MAb CL2 are coated onto microtiter plates by known procedures. Then, sera or plasma of HIV-1 infected patients are added to the precoated wells, whereupon anti-HIV-1 antibodies captured by the HIV-1 specific peptide fragments and/or by said antiidiotypic antibodies are detected by an anti-human IgG specific antibody conjugate (e.g. IgG-horseradish peroxidase) in an ELISA. The presence of antibodies that bind to HIV-1 specific peptide fragments indicate an infection with HIV.

EXAMPLE 12
Detection of HIV-infection by Means of Anti-HIV Antibodies

PBMC from HIV-1 endangered or infected patients are isolated by a Ficoll® density gradient centrifugation. Cells are then incubated with at least one of the HIV-1 neutralizing antibodies MAb CL1, MAb CL2, MAb CL3 and MAb CL4 and/or with functionally equivalent antibodies obtained upon active immunization of an anmial or human individual with an antiidiotypic antibody such as MAb CL6 (M1G1) or MAb CL5 (M1A3). Incubation is carried out at standard conditions e.g., at room temperature or at 37° C. for about one hour, or at 4° C. overnight. Bound antibody, confirming an HIV infection, is detected by a fluorochrome conjugated anti-human IgG antibody and analyzed in a fluorescence activated cell scanner (FACS).

We claim:

1. A peptide fragment which consists of one or both amino acid sequences that correspond to amino acid positions 79 to 184 or 326 to 400 (SEQ ID NO:9) of processed gp120 of HIV-1 isolate BH10 (GenBank accession M15654 (SEQ ID NOS:1–10); numbering described in the Swissprot database entry ENV$HIV10).

2. The peptide fragment according to claim 1 in combination with a pharmaceutically acceptable carrier.

3. The peptide fragment according to claim 1, linked to a carrier.

4. The peptide fragment according to claim 3, wherein said carrier is a virus or part of a virus.

5. The peptide fragment according to claim 4, wherein said part of a virus is selected from the group consisting of hemagglutinin of influenza virus, surface antigen of hepatitis B virus, surface protein of rhinovirus, surface protein of poliovirus, surface protein of Sindbis virus, and surface protein of coxsackie virus.

6. A pharmaceutical composition comprising at least one peptide fragment as defined in claim 1 or claim 3.

7. A pharmaceutical composition according to claim 6, which comprises said at least one peptide fragment in an amount suitable for administration of 0.5 to 10 μg/kg of body weight.

8. A peptide fragment comprising one or both amino acid sequences that correspond to amino acid positions 79 to 184 or 326 to 400 (SEQ ID NO:9) of processed gp120 of HIV-1 isolate BH10 (GenBank accession M15654 (SEQ ID NOS:1–10); numbering as described in the Swissprot database entry ENV$HIV10), wherein the peptide fragment in its glycosylated stage binds an HIV-1 neutralizing antibody produced by cell line CL2 (ECACC Accession No. 93091517) or cell line CL3 (ECACC Accession No. 95032235).

* * * * *